United States Patent
Souhami et al.

(10) Patent No.: US 11,026,999 B2
(45) Date of Patent: Jun. 8, 2021

(54) INSULIN GLARGINE/LIXISENATIDE FIXED RATIO FORMULATION

(71) Applicant: SANOFI-AVENTIS DEUTSCHLAND GMBH, Frankfurt am Main (DE)

(72) Inventors: Elisabeth Souhami, Paris (FR); Louise Silvestre, Paris (FR)

(73) Assignee: SANOFI-AVENTIS DEUTSCHLAND GMBH

(*) Notice: Subject to any disclaimer, the term of this patent is extended or adjusted under 35 U.S.C. 154(b) by 0 days.

(21) Appl. No.: 16/374,536

(22) Filed: Apr. 3, 2019

(65) Prior Publication Data

US 2020/0038488 A1 Feb. 6, 2020

Related U.S. Application Data

(62) Division of application No. 15/657,683, filed on Jul. 24, 2017, now abandoned, which is a division of application No. 14/303,895, filed on Jun. 13, 2014, now abandoned.

(30) Foreign Application Priority Data

Jun. 17, 2013 (EP) .................................... 13172341
Nov. 12, 2013 (EP) .................................... 13192556

(51) Int. Cl.
*A61K 38/26* (2006.01)
*A61K 38/28* (2006.01)

(52) U.S. Cl.
CPC .............. *A61K 38/28* (2013.01); *A61K 38/26* (2013.01)

(58) Field of Classification Search
None
See application file for complete search history.

(56) References Cited

PUBLICATIONS

Clinical Trial Study NCT00975286, accessed Nov. 25, 2018 at URL clinicaltrials.gov/ct2/history/NCT00975286?V_26=View#StudyPageTop; Archive date May 7, 2012, pp. 1-20 (Year: 2012).*
Lantus prescribing information, sanofi-aventis U.S. LLC, pp. 1-24, Jun. 2009 (Year: 2009).*
Riddle et al., "AddingOnce-DailyLixisenatideforType2 Diabetes Inadequately Controlled With Newly Initiated and Continuously Titrated Basal Insulin Glargine," Diabetes Care 36:2497-2503 (2013) (Year: 2013).*

* cited by examiner

*Primary Examiner* — Julie Ha
*Assistant Examiner* — Kristina M Hellman
(74) *Attorney, Agent, or Firm* — Lathrop GPM LLP; James V. DeGiulio, Esq.

(57) ABSTRACT

The present invention refers to a pharmaceutical composition comprising (a) lixisenatide or/and a pharmaceutically acceptable salt thereof, and (b) insulin glargine or/and a pharmaceutically acceptable salt thereof, wherein the compound (b) and compound (a) are present in a fixed ratio.

3 Claims, 5 Drawing Sheets

Specification includes a Sequence Listing.

INSULIN GLARGINE/LIXISENATIDE FIXED RATIO FORMULATION

This application is a divisional of U.S. patent application Ser. No. 15/657,683, filed Jul. 24, 2017, which is a divisional of U.S. patent application Ser. No. 14/303,895, filed Jun. 13, 2014, which claims the benefit of European Patent Application Nos. 13192556.2, filed Nov. 12, 2013, and 13172341.3, filed Jun. 17, 2013, the entire disclosures of which are herein incorporated by reference in their entirety.

DESCRIPTION

Subject of the present invention is a pharmaceutical composition comprising (a) lixisenatide or/and a pharmaceutically acceptable salt thereof, and (b) insulin glargine or/and a pharmaceutically acceptable salt thereof, wherein the compound (b) and compound (a) are present in a ratio of about 1.6 to about 2.4 U of compound (b) per µg of compound (a).

In a healthy person the release of insulin by the pancreas is strictly coupled to the concentration of blood glucose. An increased level of blood glucose, as appears after meals, is rapidly counterbalanced by a respective increase in insulin secretion. In fasting condition the plasma insulin level drops to a basal value which is sufficient to ensure the continuous supply of glucose to insulin-sensitive organs and tissues and to keep the hepatic glucose production at a low level at night.

In contrast to diabetes type 1, there is not generally a lack of insulin in diabetes type 2 but in many cases, particularly in progressive cases, the treatment with insulin is regarded as the most suitable therapy, if required in combination with orally administered anti-diabetic drugs.

An increased glucose level in the blood over several years without initial symptoms represents a significant health risk. It could clearly be shown by the large-scale DCCT study in the USA (The Diabetes Control and Complications Trial Research Group (1993) N. Engl. J. Med. 329, 977-986) that chronically increased levels of blood glucose are a main reason for the development of diabetes complications. Examples for diabetes complications are micro and macrovascular damages that possibly manifest themselves in retinopathies, nephropathies or neuropathies and lead to blindness, renal failure and the loss of extremities and are accompanied by an increased risk of cardiovascular diseases. It can thus be concluded that an improved therapy of diabetes primarily has to aim keeping blood glucose in the physiological range as closely as possible.

A particular risk exists for overweight patients suffering from diabetes type 2, e.g. patients with a body mass index (BMI) 30. In these patients the risks of diabetes overlap with the risks of overweight, leading e.g. to an increase of cardiovascular diseases compared with diabetes type 2 patients being of a normal weight. Thus, it is particularly necessary to treat diabetes in these patients while reducing the overweight.

Metformin is a biguanide hypoglycemic agent used in the treatment of non-insulin-dependent diabetes mellitus (diabetes mellitus type 2) not responding to dietary modification. Metformin improves glycemic control by improving insulin sensitivity and decreasing intestinal absorption of glucose. Metformin is usually administered orally. However, control diabetes mellitus type 2 in obese patients by metformin may be insufficient. Thus, in these patients, additional measures for controlling diabetes mellitus type 2 may be required.

The compound desPro$^{36}$Exendin-4(1-39)-Lys6-NH$_2$ (AVE0010, lixisenatide) is a derivative of Exendin-4. Lixisenatide is disclosed as SEQ ID NO:93 in WO 01/04156:

SEQ ID NO: 1: Lixisenatide (44 amino acids)
H-G-E-G-T-F-T-S-D-L-S-K-Q-M-E-E-E-A-V-R-L-F-I-E-W-

L-K-N-G-G-P-S-S-G-A-P-P-S-K-K-K-K-K-K-NH$_2$

SEQ ID NO: 2: Exendin-4 (39 amino acids)
H-G-E-G-T-F-T-S-D-L-S-K-Q-M-E-E-E-A-V-R-L-F-I-E-W-

L-K-N-G-G-P-S-S-G-A-P-P-P-S-NH$_2$

Exendins are a group of peptides which can lower blood glucose concentration. The Exendin analogue lixisenatide is characterised by C-terminal truncation of the native Exendin-4 sequence. Lixisenatide comprises six C-terminal lysine residues not present in Exendin-4.

In the context of the present invention, lixisenatide includes pharmaceutically acceptable salts thereof. The person skilled in the art knows pharmaceutically acceptable salts of lixisenatide. A preferred pharmaceutically acceptable salt of lixisenatide employed in the present invention is acetate.

Insulin glargine is $31^B$-$32^B$-Di-Arg human insulin, an analogue of human insulin, with further substitution of asparagine in position A21 by glycine. Insulin glargine is also termed Gly(A21)-Arg(B31)-Arg(B32)-human insulin. In the present invention, insulin glargine includes pharmaceutically acceptable salts thereof.

Insulin glargine is disclosed in U.S. Pat. No. 5,656,722.

Lantus® is an insulin product containing insulin glargine providing 24 hours basal insulin supply after single dose subcutaneous injection.

A dose of 100 U insulin glargine requires injection of 1 mL Lantus® U100, each mL Lantus® U100 contains 100 U insulin glargine. 100 U insulin glargine correspond to 3.6378 mg insulin glargine.

WO 2011/147980 discloses an on-site mixture comprising a fixed concentration of insulin glargine and a variable concentration of lixisenatide. This document also discloses an exemplary on-site mixed preparation containing 100 U/mL insulin glargine and 66.67 µg/mL (or 800/300*25 µg/ml) lixisenatide, 60.6 µg/mL (or 800/330*25 µg/mL) lixisenatide, 55.56 µg/mL (or 800/360*25 µg/mL) lixisenatide, 51.28 µg/mL lixisenatide (or 800/390*25 µg/mL lixisenatide), 47.62 µg/mL (or 800/420*25) lixisenatide, 44.44 µg/mL (or 800/450*25 µg/mL) lixisenatide, 41.67 µg/mL (or 800/480*25 µg/mL) lixisenatide or 39.22 µg/mL (or 800/510*25 µg/mL) lixisenatide.

In Example 1 of the present invention, the efficacy of a formulation comprising 100 U/mL insulin glargine and 50 µg/mL lixisenatide was tested in comparison with a formulation comprising 100 U/mL insulin glargine in diabetes type 2 patients.

It has been demonstrated that in the combination group (treated with the insulin glargine/lixisenatide fixed ratio formulation) the final daily dose at the end of the treatment period was reduced compared with the group receiving the formulation to reach a fasting self-monitored plasma glucose concentration between ≥80 and ≤100 mg/dL. In the combination group 0% received a dose of >60 U/30 µg, and 42.2% received a dose of >40 U/20 µg and ≤60 U/30 µg. In the control group 28.4% of the patients received a dose of >40 U/20 µg and ≤60 U/30 µg, and 16.7% of the patients received a dose of >60 U/30 µg. In the combination group, 14.3% of the patients received a dose <20 U/10 µg, whereas only 9.9% of the control patients received this dose (Table 6).

Furthermore, treatment with insulin glargine/lixisenatide fixed ratio combination significantly improved postprandial glycemic control in comparison to insulin glargine as shown by the results for the 2-hour PPG assessment and for 2-hour glucose excursion. In addition, patients treated with insulin glargine/lixisenatide fixed ratio combination had a statistically significant greater decrease in average 7-point self-monitored plasma glucose (SMPG) profile compared with patients treated with insulin glargine.

A statistically significant difference in the body weight change from baseline to week 24 was found between the 2 treatment groups: body weight decreased in the insulin glargine/lixisenatide fixed ratio combination group and increased in the insulin glargine group.

A higher percentage of patients in the combination group reached target HbA1c≤6.5% (71.9% versus 64.6%) or <7% (84.4% versus 78.3%) as compared with the insulin glargine group (Table 8).

In summary, the insulin glargine/lixisenatide fixed ratio combination results in an improvement of glycemic control and body weight by a reduced dose of insulin glargine, compared with insulin glargine alone. This demonstrates the superiority of an insulin glargine/lixisenatide fixed ratio combination versus insulin glargine.

Example 2 describes a randomized, 30 week, active-controlled, open-label, 3-treatment arm, parallel-group multicenter study comparing the efficacy and safety of insulin glargine/lixisenatide fixed ratio combination of the present invention to insulin glargine alone and to lixisenatide alone on top of metformin in patients with type 2 diabetes mellitus (T2DM).

One aspect of the present invention is a pharmaceutical composition comprising
  (a) Lixisenatide (desPro$^{36}$Exendin-4(1-39)-Lys$_6$-NH$_2$) or/and a pharmaceutically acceptable salt thereof, and
  (b) insulin glargine or/and a pharmaceutically acceptable salt thereof,
  wherein the compound (b) and compound (a) are present in a ratio of about 1.6 to about 2.4 U of compound (b) per µg of compound (a).

Compound (b) and compound (a) can also be present in a ratio of about 1.8 to about 2.2 U of compound (b) per µg of compound (a). Compound (b) and compound (a) can also be present in a ratio of about 1.9 to about 2.1 U of compound (b) per µg of compound (a). Compound (b) and compound (a) can also be present in a ratio of about 2 U of compound (b) per µg of compound (a).

The concentration ratio of compound (b) to compound (a) in the pharmaceutical composition of the present invention is a fixed ratio.

In the present invention, compound (a) and compound (b) are provided in a single composition in a pre-determined fixed ratio. Also within the scope of the present invention are two separate compositions, the first composition comprising compound (a) and the second composition comprising compound (b), to be administered to a patient in need thereof as defined herein, in a fixed ratio as defined herein.

In the composition of the present invention, the concentration of compound (a) can be in the range of 40-60 µg/ml. The concentration ratio of compound (b) to compound (a) can be in the range of 1.6 to 2.4 U/µg, 1.8 to 2.2 U/µg, 1.9 to 2.1 U/µg or about 2 U/µg.

In the composition of the present invention, the concentration of compound (b) can be in the range of 64-144 U/ml, 72-132 U/ml, 76-126 U/ml or 80-120 U/ml.

In the composition of the present invention, the concentration of compound (a) can be in the range of 40-60 µg/ml, and the concentration of compound (b) can be in the range of 64-144 U/ml, 72-132 U/ml, 76-126 U/ml or 80-120 U/ml.

In the composition of the present invention, the concentration of compound (a) can be in the range of 45-55 µg/ml. The concentration ratio of compound (b) to compound (a) can be in the range of 1.6 to 2.4 U/µg, 1.8 to 2.2 U/µg, 1.9 to 2.1 U/µg or about 2 U/µg.

In the composition of the present invention, the concentration of compound (b) can be in the range of 72-132 U/ml, 81-121 U/ml, 85.5-115.5 U/ml, or 90-110 U/ml.

In the composition of the present invention, the concentration of compound (a) can be in the range of 45-55 µg/ml, and the concentration of compound (b) can be in the range of 72-132 U/ml, 81-121 U/ml, 85.5-115.5 U/ml, or 90-110 U/ml.

In the pharmaceutical composition, the concentration of compound (a) can also be about 50 µg/ml. The concentration ratio of compound (b) to compound (a) can be in the range of 1.6 to 2.4 U/µg, 1.8 to 2.2 U/µg, 1.9 to 2.1 U/µg or about 2 U/µg. The concentration of compound (b) can be in the range of 80-120 U/ml, 90-110 U/ml, 95-105 U/ml, or can be about 100 U/ml.

In particular, in the composition of the present invention the concentration of compound (a) is about 50 µg/ml, and the concentration of compound (b) is about 100 U/ml.

The pharmaceutical composition preferably is not an on-site mixed composition or formulation. The on-site mixed composition or formulation is prepared "on-site", for example shortly before administration. In this context, an on-site mixed composition or formulation can be a composition or formulation prepared from at least two separate compositions, each comprising at least one of lixisenatide and insulin glargine. In particular, an on-site mixed formulation or composition is a composition prepared from two separate compositions, the first composition comprising lixisenatide and insulin glargine, and the second composition comprising insulin glargine. More particular, the on-site mixed composition or formulation can comprise a fixed volume of the first composition and a variable volume of the second composition.

If the pharmaceutical composition comprises compound (a) in a concentration range of 40 to 60 µg/ml, the concentration of compound (a) preferably is not a concentration selected from 55.56 µg/mL, 51.28 µg/mL, 47.62 µg/mL, 44.44 µg/mL, and 41.67 µg/mL.

In the concentration range of 40 to 60 µg/ml, the concentration of compound (a) preferably is not a concentration selected from 800/360*25 µg/mL, 800/390*25 µg/mL, 800/420*25 µg/mL, 800/450*25 µg/mL, and 800/480*25 µg/mL.

If the pharmaceutical composition comprises compound (a) in a concentration range of 45 to 55 µg/ml, the concentration of compound (a) is preferably not a concentration selected from 51.28 µg/mL and 47.62 µg/mL. In the concentration range of 45 to 55 µg/ml, the concentration of compound (a) preferably is not a concentration selected from 800/390*25 µg/mL and 800/420*25 µg/mL.

The composition of the present invention can be used for the treatment of diabetes mellitus type 1 or/and 2 patients, or/and for the treatment of conditions associated with diabetes type diabetes mellitus type 1 or/and 2.

In particular the composition of the present invention can be used for the treatment of diabetes mellitus type 2 patients, or/and for the treatment of conditions associated with diabetes type diabetes mellitus type 2. Such conditions include a decrease of glucose tolerance, an increased postprandial plasma glucose concentration, an increase in fasting plasma glucose concentration, or/and an increased HbA1c value, compared for example with persons not suffering from diabetes type 2.

The composition of the present invention can be used in glycemic control in diabetes type 2 patients. As demonstrated by Example 1 of the present invention, the composition as described herein can be used for improving glycemic control. In the present invention, "improvement of glycemic control" or "glycemic control" in particular refers to improvement of glucose tolerance, improvement of postprandial plasma glucose concentration, improvement of fasting plasma glucose concentration, or/and improvement of the HbA1c value.

In particular, improvement of glucose tolerance includes improvement of the postprandial plasma glucose concentration, improvement of the postprandial plasma glucose excursion or/and improvement of fasting plasma glucose concentration. More particular, improvement of glucose tolerance includes improvement of the postprandial plasma glucose concentration.

In particular, improvement of postprandial plasma glucose concentration is reduction of the postprandial plasma glucose concentration. Reduction means in particular that the plasma glucose concentration reaches normoglycemic values or at least approaches these values.

In particular, improvement of postprandial plasma glucose excursion is reduction of the postprandial plasma glucose excursion. Reduction means in particular that the plasma glucose excursion reaches normoglycemic values or at least approaches these values.

In particular, improvement of fasting plasma glucose concentration is reduction of the fasting plasma glucose concentration. Reduction means in particular that the plasma glucose concentration reaches normoglycemic values or at least approaches these values.

In particular, improvement of the HbA1c value is reduction of the HbA1c value. Reduction of the HbA1c value in particular means that the HbA1c value is reduced below 6.5% or 7%, for example after treatment for at least one month, at least two months, at least three months, at least four months, at least five months, at least six months or at least one year.

The pharmaceutical composition of the present invention may be administered as add-on to the treatment with metformin or/and a pharmaceutically acceptable salt thereof. Metformin is the international nonproprietary name of 1,1-dimethylbiguanide (CAS Number 657-24-9). In the present invention, the term "metformin" includes any pharmaceutically acceptable salt thereof.

In the present invention, metformin may be administered orally. The skilled person knows formulations of metformin suitable for treatment of diabetes type 2 by oral administration. Metformin may be administered to a patient in need thereof, in an amount sufficient to induce a therapeutic effect. Metformin may be administered in a dose of at least 1.0 g/day or at least 1.5 g/day. For oral administration, metformin may be formulated in a solid dosage form, such as a tablet or pill. Metformin may be formulated with suitable pharmaceutically acceptable carriers, adjuvants, or/and auxiliary substances.

In the present invention, the terms "add-on", "add-on treatment", "add-on therapy" and "on top of" relate to treatment of diabetes mellitus type 2 with the metformin and the composition of the present invention, as described herein. The composition of the present invention and metformin may be administered by different administration routes. Metformin may be administered orally, and the composition of the present invention may be administered parenterally.

The patient to be treated by the composition of the present invention may be a patient suffering from diabetes type 2.

The patient to be treated by the composition of the present invention suffering from diabetes type 2 may be a patient suffering from diabetes type 2, wherein diabetes type 2 is not adequately controlled by treatment with metformin alone, for example by treatment with metformin for at least 2 or at least 3 months, for example with a dose of at least 1.0 g/day or at least 1.5 g/day of metformin. In particular, the diabetes type 2 is not adequately controlled by treatment with metformin alone at the onset of treatment with the composition of the present invention.

The patient to be treated by the composition of the present invention suffering from diabetes type 2 may be a patient suffering from diabetes type 2, wherein diabetes type 2 is not adequately controlled by treatment with insulin glargine alone, for example by treatment with insulin glargine for at least 2 or at least 3 months. In particular, the diabetes type 2 is not adequately controlled by treatment with insulin glargine alone at the onset of treatment with the composition of the present invention.

The patient to be treated by the composition of the present invention suffering from diabetes type 2 may be a patient suffering from diabetes type 2, wherein diabetes type 2 is not adequately controlled by treatment with lixisenatide alone, for example by treatment with lixisenatide for at least 2 or at least 3 months. In particular, the diabetes type 2 is not adequately controlled by treatment with lixisenatide alone at the onset of treatment with the composition of the present invention.

The patient to be treated by the composition of the present invention suffering from diabetes type 2 may be a patient suffering from diabetes type 2, wherein diabetes type 2 is not adequately controlled by treatment with metformin and insulin glargine alone, or with metformin and lixisenatide alone, for example by treatment for at least 2 or at least 3 months. In particular, the diabetes type 2 is not adequately controlled by treatment with metformin and insulin glargine alone, or with metformin and lixisenatide alone at the onset of treatment with the composition of the present invention.

In the present invention, a patient the diabetes type 2 of which is not adequately controlled if at least one physiological parameter describing blood glucose concentration (i.e. the HbA1c value, the postprandial plasma glucose concentration, the postprandial plasma glucose excursion, or/and the fasting plasma glucose concentration) exceeds normoglycemic values, as described herein. In particular, a patient the diabetes type 2 of which is not adequately controlled may have (i) a HbA1c value in the range of 7% to 10% or even larger, (ii) a postprandial glucose excursion, in particular a 2-hour postprandial glucose excursion, of at least 2 mmol/L, (iii) a postprandial plasma glucose concentration, in particular a 2-hour postprandial glucose concentration, of at least 10 mmol/L, or/and (iv) a fasting plasma glucose of at least 7.0 mmol/L or 8.0 mmol/L.

The patient to be treated by the composition of the present invention suffering from diabetes type 2 may be an obese patient. In the present invention, an obese patient may have a body mass index of at least 30 kg/m², at least 31 kg/m², at least 32 kg/m² or at least 33 kg/m².

The patient to be treated by the composition of the present invention suffering from diabetes type 2 may have a normal body weight. In the present invention, a patient having normal body weight may have a body mass index in the range of 17 kg/m² to 25 kg/m², 17 kg/m² to <30 kg/m² or <30 kg/m².

The patient to be treated by the composition of the present invention may be an adult patient. The patient may have an age of at least 18 years of may have an age in the range of 18 to 80 years, of 18 to 50 years, or 40 to 80 years, or 50 to 60 years. The patient may be at least 50 years old. The patient may be younger than 50 years.

The patient to be treated by the composition of the present invention may be a patient who does not receive an antidiabetic treatment, for instance by insulin or/and related compounds, metformin or GLP-1 agonists such as lixisenatide. In particular, the patient to be treated does not receive a GLP-1 receptor agonist or/and an insulin.

The patient to be treated by the composition of the present invention may suffer from diabetes mellitus type 2 for at least 1 year or at least 2 years. In particular, in the diabetes type 2 patient, diabetes mellitus type 2 has been diagnosed at least 1 year or at least 2 years before onset of therapy by the composition of the present invention.

The diabetes type 2 patient may have a HbA1c value of at least about 9%, at least 8%, at least about 7.5%, or at least 7.0% at the onset of the treatment with the composition. The patient may also have a HbA1c value of about 7% to about 10% at the onset of the treatment with the composition. Example 1 of the present invention demonstrates that treatment by lixisenatide results in a reduction of the $HbA_{1c}$ value in diabetes type 2 patients.

In yet another aspect of the present invention, the composition as described herein can be used for improving the $HbA_{1c}$ value in a patient suffering from diabetes type 2, as described herein.

In yet another aspect of the present invention, the composition as described herein can be used for improving glucose tolerance in a patient suffering from diabetes type 2, as described herein. Example 1 of the present invention demonstrates an improved 2-hour glucose excursion.

In yet another aspect of the present invention, the composition as described herein can be used for improving postprandial plasma glucose concentration in a patient suffering from diabetes type 2, as described herein. Example 1 of the present invention demonstrates an improved 2-hour postprandial glucose concentration.

In yet another aspect of the present invention, the composition as described herein can be used for improving postprandial plasma glucose excursion, in particular the 2-hour postprandial glucose excursion, in a patient suffering from diabetes type 2, as described herein.

In yet another aspect of the present invention, the composition as described herein can be used for improving fasting plasma glucose concentration in a patient suffering from diabetes type 2, as described herein.

In yet another aspect of the present invention, the composition as described herein can be used for improving average 7-point SMPG profile. Example 1 of the present invention demonstrates an improved average 7-point SMPG profile by administration of the composition of the present invention to diabetes type 2 patients. Self-monitored plasma glucose (SMPG), as used herein, is in particular the "7-point Self Monitored Plasma Glucose". "7-point Self Monitored Plasma Glucose" in particular refers to the measurement of plasma glucose seven times a day and calculation of the average plasma glucose concentration therefrom. The "7-point Self Monitored Plasma Glucose" value is in particular an average plasma glucose concentration including fasting and postprandial conditions. In particular, measurements of plasma glucose concentration are performed pre-breakfast, post-breakfast (e.g. 2-hour post-breakfast), pre-lunch, post-lunch (e.g. 2-hour post-lunch), pre-dinner, post-dinner (e.g. 2-hour post-dinner) and at bedtime (see also FIG. 3). The treatment by the combination of the present invention, as described herein, can improve the self-monitored plasma glucose.

In yet another aspect of the present invention, the composition as described herein can be used for improving body weight in a patient suffering from diabetes type 2, as described herein. Example 1 of the present invention demonstrates in improvement of body weight by administration of the composition of the present invention.

In the present invention, normoglycemic values are blood glucose concentrations of in particular 60-140 mg/dl (corresponding to 3.3 bis 7.8 mM/L). This range refers in particular to blood glucose concentrations under fasting conditions or/and postprandial conditions.

The diabetes type 2 patient may have a 2-hour postprandial plasma glucose concentration of at least 10 mmol/L, at least 12 mmol/L, at least 13 mmol/L, at least 14 mmol/L, at least 15 mmol/L, at least 16 mmol/L, or at least 17 mmol/L at the onset of the treatment with the composition of the present invention. These plasma glucose concentrations exceed normoglycemic concentrations.

The diabetes type 2 patient may have a glucose excursion (in particular a 2-hour postprandial glucose excursion of at least 2 mmol/L, at least 3 mmol/L, at least 4 mmol/L, at least 5 mmol/L, at least 5.5 mmol/L, at least 6 mmol/L, at least 6.5 mmol/L, or at least 7 mmol/L at the onset of the treatment with the composition of the present invention. In the present invention, the glucose excursion is in particular the difference of the 2-hour postprandial plasma glucose concentration and the plasma glucose concentration 30 minutes prior to a meal test.

"Postprandial" is a term that is well known to a person skilled in the art of diabetology. The term "postprandial" describes in particular the phase after a meal or/and exposure to glucose under experimental conditions. In a healthy person this phase is characterised by an increase and subsequent decrease in blood glucose concentration. The term "postprandial" or "postprandial phase" typically ends up to 2 h after a meal or/and exposure to glucose.

The diabetes type 2 patient as disclosed herein may have a fasting plasma glucose concentration of at least 7 mmol/L, at least 8 mmol/L, at least 9 mmol/L, at least 10 mmol/L, or at least 11 mmol/L at the onset of the treatment with the composition of the present invention. These plasma glucose concentrations exceed normoglycemic concentrations at the onset of the treatment with the composition of the present invention.

The diabetes type 2 patient as disclosed herein may have a self-monitored plasma glucose concentration of at least 8 mmol/L, at least 9 mmol/L, at least 10 mmol/L, or at least 11 mmol/L at the onset of the treatment with the composition of the present invention.

In the present invention, the composition as described herein may be administered to a patient in need thereof, in an amount sufficient to induce a therapeutic effect.

In the present invention, the composition as described herein may comprise at least one of suitable pharmaceutically acceptable carriers, adjuvants, or/and auxiliary substances.

The composition as described herein may be administered parenterally, e.g. by injection (such as by intramuscular or by subcutaneous injection). Suitable injection devices, for instance the so-called "pens" comprising a cartridge comprising the active ingredient, and an injection needle, are known.

The pharmaceutical composition of the present invention can be provided within a container, for example an ampoule, a vial or a "pen", as described herein, to be used by the patient. For example, the pharmaceutical composition being a liquid formulation can be provided within a vial. From such vial, the patient can draw up the required dose into a syringe (in particular a single-use syringe).

The composition as described herein may be administered in a suitable amount.

The dosage of the composition of the present invention may be determined by one of the active agents of the composition to be administered, i.e. by the amount of insulin glargine or by the amount of lixisenatide. It is contemplated that in this case, the second active agent of the composition is administered in an amount defined by the fixed-dose ratio of the composition.

The dose of the composition of the present invention may be determined by the amount of lixisenatide to be administered.

In the present invention, the composition as described herein may be administered in an amount in the range of 10 to 15 μg lixisenatide per dose or 15 to 20 μg lixisenatide per dose.

In the present invention, the composition as described herein may be administered in a daily dose in the range of 10 to 20 μg lixisenatide, in the range of 10 to 15 μg lixisenatide, or in the range of 15 to 20 μg lixisenatide.

The composition as described herein may be administered by one injection per day.

The pharmaceutical composition of the present invention may be administered in a dose of 0.05 to 0.5 μg/kg body weight lixisenatide.

The dose of the composition of the present invention may also be determined by the amount of insulin glargine required. For example, the insulin glargine dose to be injected may be 40 U or less, or in a range from 10 to 40 U insulin glargine or 20 U to 40 U insulin glargine. The insulin glargine dose to be injected may also be 60 U or less, or in a range from 10 U to 60 U insulin glargine or 30 U to 60 U insulin glargine. The daily insulin glargine dose to be injected may be 40 U or less, or in a range from 10 to 40 U insulin glargine or 20 U to 40 U insulin glargine. The daily insulin glargine dose to be injected also may be 60 U or less, or in a range from 10 U to 60 U insulin glargine or 30 U to 60 U insulin glargine.

The composition of the present invention may be administered in a dose of 0.25 to 1.5 U/kg body weight insulin glargine.

In the present invention, the composition as described herein may be a liquid composition. The skilled person knows liquid compositions of lixisenatide suitable for parenteral administration. The skilled person also knows liquid compositions of insulin glargine suitable for parenteral administration. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. The pH may be adjusted by a pharmaceutically acceptable diluted acid (typically HCl) or pharmaceutically acceptable diluted base (typically NaOH).

The liquid composition of the present invention may comprise a suitable preservative. A suitable preservative may be selected from phenol, m-cresol, benzyl alcohol and p-hydroxybenzoic acid ester. A preferred preservative is m-cresol.

The liquid composition of the present invention may comprise a tonicity agent. A suitable tonicity agent may be selected from glycerol, lactose, sorbitol, mannitol, glucose, NaCl, calcium or magnesium containing compounds such as CaCl2). The concentration of glycerol, lactose, sorbitol, mannitol and glucose may be in the range of 100-250 mM. The concentration of NaCl may be up to 150 mM. A preferred tonicity agent is glycerol.

The liquid composition of the present invention may comprise methionine from 0.5 μg/ml to 20 μg/ml, preferably from 1 μg/ml to 5 μg/ml. Preferably, the liquid composition comprises L-methionine.

Yet another aspect of the present invention refers to a method of treatment of a medical indication, disease or condition, as described herein. For example, the method may comprise the administration of the composition as described herein. The method may be a method of treatment of diabetes type 2 patients, or/and of treatment of conditions associated with diabetes type 2, as described herein. The patient may be a patient as defined herein.

A further aspect of the present invention is a method for improvement of glycemic control in diabetes type 2 patients, said method comprising administering the composition of the present invention to a patient in need thereof. In the method of the present invention, the patient may be the patient defined herein.

Yet another aspect of the present invention refers to the use of the composition as described herein for the manufacture of a composition for the treatment of a medical indication, disease or condition, as described herein. For example, the composition of the present invention can be used for the manufacture of a composition for the treatment of diabetes type 2 patients, or/and for the treatment of conditions associated with diabetes type 2. In particular, the composition of the present invention can be used for the manufacture of a composition for the improvement of glycemic control, improvement of glucose tolerance, improvement of postprandial plasma glucose concentration, improvement of postprandial plasma glucose excursion, improvement of fasting plasma glucose concentration, or/and improvement of the HbA1c value. The patient may be a patient as defined herein.

The invention is further illustrated by the following examples and figures.

EXAMPLE 1

Figure 1:
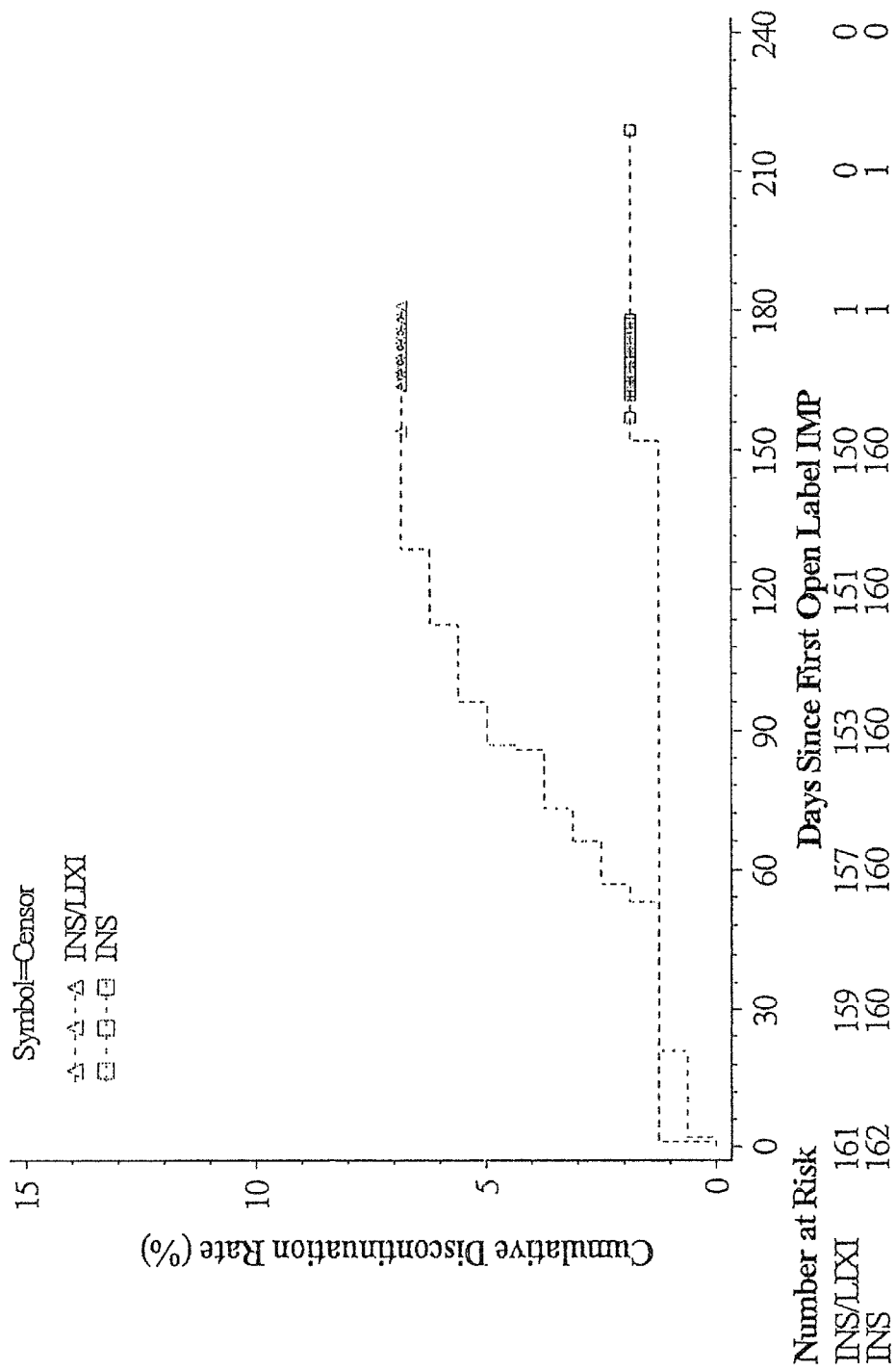
FIG. 1—Kaplan-Meier cumulative incidence curve for time to treatment discontinuation due to any reason—Randomized population. INS/LIXI=Insulin Glargine/Lixisenatide Fixed Ratio Combination, INS=Insulin Glargine.

A randomized, 24-week, open-label, 2-arm parallel-group, multicenter study comparing the efficacy and safety of insulin glargine/lixisenatide fixed ratio combination versus insulin glargine on top of metformin in type 2 diabetic patients.

1 Abbreviations

AE: Adverse event
ANCOVA: Analysis of covariance
BMI: Body mass index
CI: Confidence interval
CMH: Cochran-Mantel-Haenszel
ECG: Electrocardiogram
FPG: Fasting plasma glucose
GFR: Glomerular filtration rate
GLP-1: Glucagon-like peptide-1
HLGT: High level group term
HLT: High level term
IMP: Investigational medicinal product
LOCF: Last observation carried forward
LS: Least squared
MDRD: Modification of diet in renal disease
mITT: Modified Intent-To-Treat
PG: Plasma glucose
PPG: Post-prandial plasma glucose
PT: Preferred term
SAE: Serious adverse event
SMPG: Self-monitored plasma glucose
SOC: System organ class
TEAE: Treatment-emergent adverse event 2 Synopsis Title of the study: A randomized, 24-week, open-label, 2-arm parallel-group, multicenter study comparing the efficacy and safety of insulin glargine/lixisenatide fixed ratio combination versus insulin glargine on top of metformin in type 2 diabetic patients.
Study center(s): Multicenter (67 centers)
Publications (reference): NA
Phase of development: Phase 2

Objectives:
Primary Objective:
To demonstrate the non-inferiority of insulin glargine/lixisenatide fixed ratio combination versus insulin glargine on glycemic control over 24 weeks, as evaluated by HbA1c reduction in type 2 diabetic patients not adequately controlled with metformin.
Secondary Objectives:
To demonstrate the superiority of insulin glargine/lixisenatide fixed ratio combination versus insulin glargine on glycemic control in relation to a meal over 24 weeks, as evaluated by 2-hour Post-prandial Plasma Glucose (PPG) and glucose excursion during a standardized meal test.
To assess the efficacy of insulin glargine/lixisenatide fixed ratio combination on:
Percentage of patients reaching HbA1c <7% or ≤6.5% at week 24
7-point Self-Monitored Plasma Glucose (SMPG) profile (each time point and mean daily value) at week 24
Body weight at week 24
Insulin glargine dose at week 24
Fasting Plasma Glucose (FPG) at week 24
Percentage of patients requiring rescue therapy during the 24-week open label treatment period
30-minute and 1-hour PPG and plasma glucose excursion during standardized meal test at week 24
Percentage of patients reaching HbA1c <7% at week 24 with no documented symptomatic hypoglycemia during the 24-week open label treatment period
Percentage of patients reaching HbA1c <7% with no weight gain at week 24
To assess safety and tolerability of insulin glargine/lixisenatide fixed ratio combination.
To assess the plasma concentration of lixisenatide (in the insulin glargine/lixisenatide fixed ratio combination group) following injection on Day 1 and at Week 24.
To assess the development of anti-lixisenatide (for insulin glargine/lixisenatide fixed ratio combination) and anti-insulin antibodies (for both treatment groups).
Methodology: This was an open-label, 1:1 randomized, active-controlled, 2-arm, 24-week duration, parallel-group study comparing:
Insulin glargine/lixisenatide fixed ratio (2 U of insulin glargine for 1 μg of lixisenatide) combination
Insulin glargine alone
The patients were stratified by screening values of HbA1c (<8, ≥8%) and Body Mass Index (BMI) (<30, ≥30 kg/m$^2$). The study comprised 3 periods: An up-to 2-week screening period; A 24-week randomized treatment period; A 3-day safety follow-up period.
Number of patients: Planned: 310
Randomized: 323
Treated: 323
Evaluated: Efficacy: 323
Safety: 323
Diagnosis and criteria for inclusion: Patients with type 2 diabetes mellitus diagnosed for at least 1 year, treated with metformin at a stable dose of at least 1.5 g/day for at least 3 months prior to screening visit, and with HbA1c ≥7%, and ≤10% at screening.
Study Treatments
Investigational medicinal products (IMPs): Insulin glargine/lixisenatide fixed ratio combination and insulin glargine.

Formulation:
Tested drug: Insulin glargine/lixisenatide fixed ratio combination (100 U/ml insulin glargine/50 μg/ml lixisenatide [ratio 2 U/1 μg]) was supplied as a sterile, aqueous solution in 3 ml cartridges to be used in a flexible dose re-usable pen (TactiPen®).
Control drug: Insulin glargine was supplied as a sterile, aqueous solution in Lantus® SoloSTAR® disposable self-injector device (3 ml of 100 U/ml).
Route of Administration:
Subcutaneous injection
Dose Regimen:
In both groups, the initial daily dose of insulin glargine to be administered during the first week of treatment was 10 U. Afterwards, the dose was adjusted to achieve a target fasting SMPG in the range of 80 to 100 mg/dL (4.4 to 5.6 mmol/L). The dose was titrated weekly until the patient reached the target fasting SMPG. Thereafter, until the end of the study, the dose was adjusted as necessary to maintain a fasting SMPG between 80 and 100 mg/dL (4.4 and 5.6 mmol/1), inclusive. Doses could be reduced or modified at any time for hypoglycemia.

In the insulin glargine/lixisenatide fixed ratio combination group, the lixisenatide dose was automatically increased or decreased following insulin glargine dose increase or decrease according to the 2 U/1 μg fixed ratio used in the combination therapy, and the maximum allowed dose of insulin glargine was 60 U (corresponding to a lixisenatide dose of 30 μg). If a 60 U/30 μg dose was not sufficient to maintain FPG/HbA1c below predefined thresholds values, the dose was to be kept at 60 U and a rescue therapy was to be introduced.

Batch Number(s):
Not applicable to the KRM
Noninvestigational medicinal product(s) (background therapy): metformin
Formulation:
Metformin ≥1.5 g/day.
Route of Administration:
Oral
Dose Regimen:
Metformin was to be kept at stable dose throughout the study unless there was a specific safety issue related to this treatment.
Batch Number(s):
Not applicable to the KRM
Duration of treatment: 24 weeks
Duration of observation: Maximum duration of approximately 27 weeks.
Criteria for Evaluation:
Efficacy:
Primary Endpoint:
Change in HbA1c from baseline to Week 24
Secondary Endpoints:
Change in 2-hour PPG during meal test from baseline to Week 24
Change in 2-hour plasma glucose excursion during meal test from baseline to Week 24
Percentage of patients reaching HbA1c ≤6.5% or <7% at Week 24
Change in 7-point SMPG profiles from baseline to Week 24 (each time point and mean daily value)
Change in body weight from baseline to Week 24, Average daily Insulin glargine dose at Week 24
Change in FPG from baseline to Week 24
Percentage of patients requiring rescue therapy during the 24-week open-label treatment period
Change in 30-minute and 1-hour PPG and plasma glucose excursion during meal test from baseline to week 24
Percentage of patients reaching HbA1c <7% at week 24 with no documented symptomatic hypoglycemia during the 24-week open label treatment period
Percentage of patients reaching HbA1c <7% with no weight gain at week 24
Safety: Adverse events, serious adverse events, symptomatic hypoglycemia, vital signs, electrocardiogram (ECG), safety laboratory values.
Antibody assessments: Not available in the KRM
Pharmacokinetics: Not available in the KRM
Statistical Methods:
Efficacy: The primary efficacy population was the modified Intent-To-Treat (mITT) population, which included all randomized patients who received at least one dose of study medication, and had both a baseline assessment and at least one post-baseline assessment of any primary or secondary efficacy variables, irrespective of compliance with the study protocol and procedures.

The primary endpoint (change in HbA1c from baseline to week 24) was analyzed using an analysis of covariance (ANCOVA) model with treatment (insulin glargine/lixisenatide fixed ratio combination, insulin glargine alone), randomization strata of screening HbA1c (<8%, ≥8%), randomization strata of screening BMI (<30 kg/m$^2$, ≥30 kg/m$^2$) and country as fixed effects and using the baseline HbA1c value as a covariate.

The non-inferiority of insulin glargine/lixisenatide fixed ratio combination to insulin glargine alone was tested using a 1-sided statistical test with alpha level of 0.025 and a non-inferiority margin of 0.4% HbA1c. The non-inferiority would be demonstrated if the upper bound of the two-sided 95% confidence interval (CI) of the difference between insulin glargine/lixisenatide fixed ratio combination and insulin glargine alone on mITT population is ≤0.4%. If non-inferiority is established, then a corresponding check of statistical superiority of insulin glargine/lixisenatide fixed ratio combination over insulin glargine alone would be performed for the primary endpoint.

All continuous secondary efficacy endpoints were analyzed using a similar ANCOVA model with treatment, randomization strata of screening HbA1c (<8%, ≥8%), randomization strata of screening BMI (<30 kg/m$^2$, ≥30 kg/m$^2$) and country as fixed effects and using the baseline value of the corresponding parameter as a covariate. Insulin glargine dose was not included in the ANCOVA model as a covariate since patients enrolled were insulin-naïve.

All categorical secondary efficacy endpoints were analyzed by using Cochran-Mantel-Haenszel (CMH) method stratified by randomization strata of screening HbA1c (<8%, ≥8%) and BMI (<30 kg/m$^2$, ≥30 kg/m$^2$).

Safety: The safety analysis was conducted on the safety population, defined as all randomized patients who received at least one dose of IMP (regardless of the amount of treatment administered). The evaluation of AEs, laboratory, vital sign, and ECG data was descriptive.

Summary:
Population characteristics: A total of 323 patients were randomized to one of the two treatment groups (161 in the insulin glargine/lixisenatide fixed ratio combination group and 162 in the insulin glargine group). All randomized patients were exposed to the study treatment and were included in the mITT population. Demographics and baseline characteristics were generally similar across the treatment groups. The median age was 58 years. The study population was primarily Caucasian (98.5%).

Efficacy Results:

The least squared (LS) mean changes from baseline to Week 24 in HbA1c were −1.82% for the insulin glargine/lixisenatide fixed ratio combination group and −1.64% for the insulin glargine group (LS mean difference vs. glargine group=−0.17%; 95% CI=−0.312% to −0.037%). Based on the pre-specified primary analysis, the non-inferiority of the insulin glargine/lixisenatide fixed ratio combination compared to the insulin glargine on HbA1c change from baseline to week 24 was demonstrated, as the upper bound of the two-sided 95% CI of the LS mean difference was less than the predefined non-inferiority margin of 0.4%. Statistical superiority of the insulin glargine/lixisenatide fixed ratio combination over insulin glargine was also demonstrated for this primary end points (LS mean difference vs. glargine group=−0.17%; p-value=0.0130).

Treatment with insulin glargine/lixisenatide fixed ratio combination significantly improved postprandial glycemic control in comparison to insulin glargine as shown by the results for the 2-hour PPG assessment (LS mean difference of −3.17 mmol/L; p-value <0.0001) and for 2-hour glucose excursion (LS mean difference of −3.24 mmol/L; p-value <0.0001). In addition, patients treated with insulin glargine/lixisenatide fixed ratio combination had a statistically significant greater decrease compared to patients treated with insulin glargine in average 7-point SMPG profile (LS mean difference of −0.30 mmol/L; p-value=0.0154).

A statistically significant difference in the body weight change from baseline to week 24 was found between the 2 treatment groups: body weight decreased in the insulin glargine/lixisenatide fixed ratio combination group and increased in the insulin glargine group (LS mean body weight change from baseline to Week 24 of −0.97 kg and +0.48 kg, respectively; LS mean difference for insulin glargine/lixisenatide fixed ratio combination versus insulin glargine was −1.44 kg; 95% CI: −2.110 kg, −0.773 kg; p<0.0001).

For average daily insulin glargine dose at Week 24 the difference between insulin glargine/lixisenatide fixed ratio combination and insulin glargine treatment groups was borderline significant (LS mean difference of −3.24 U; 95% CI: [−6.592 U to 0.114 U]; p=0.0583). Similar reduction in mean change FPG from baseline to Week 24 (LS mean: −3.35 mmol/L in the combination group; −3.51 mmol/L in insulin glargine group) was observed. Only 1 patient (in the insulin glargine group) required rescue therapy.

Safety Results:

Insulin glargine/lixisenatide fixed ratio combination was overall well tolerated. Slightly more patients in the insulin glargine/lixisenatide fixed ratio combination group (86 [53.4%]) reported treatment emergent adverse events (TEAEs) than in the insulin glargine group (82 [50.6%]). The most frequently reported TEAE in the combination group was nausea (12 [7.5%] versus 0 in the insulin glargine group).

Fifteen patients (9 [5.6%] for the combination group and 6 [3.7%] for the insulin glargine group) had treatment emergent serious adverse events (SAEs) which were distributed over a variety of system organ classes (SOCs) without a notable increase in any specific SOC. Six (3.7%) patients treated with the combination and none receiving insulin glargine had TEAEs leading to treatment discontinuation: for 2 of these patients, TEAEs leading to treatment discontinuation were from the gastrointestinal disorders SOC (nausea and/or vomiting).

No death was reported in this study.

A total of 2 patients (1 [0.6%] in each group) reported 6 events adjudicated as allergic reactions by the Allergic Reaction Assessment Committee (ARAC). None was adjudicated as possibly related to the IMP. A total of 5 (3.1%) patients in the combination group and 1 (0.6%) in the insulin glargine group) experienced injection site reactions, none of them being considered serious or severe or leading to treatment discontinuation.

No TEAE of pancreatitis or increased calcitonin 20 µg/mL was reported in the study.

Forty (24.8%) patients treated with the combination had 81 symptomatic hypoglycemia events (including documented, severe, and probable symptomatic hypoglycemia) as compared to 40 (24.7%) patients with 84 events in the insulin glargine group. The number of events per patient-year in symptomatic hypoglycemia was 1.11 in both treatment groups. No severe symptomatic hypoglycemia was reported.

Preliminary Conclusions:

In these patients with T2DM uncontrolled on metformin, the non-inferiority of the insulin glargine/lixisenatide fixed ratio combination compared to the insulin glargine on HbA1c change from baseline to week 24 was demonstrated, as the upper bound of the two-sided 95% CI of the LS mean difference was less than the predefined non-inferiority margin of 0.4%. Statistical superiority of the insulin glargine/lixisenatide fixed ratio combination over insulin glargine was also demonstrated for this primary endpoint.

Compared to insulin glargine, treatment with insulin glargine/lixisenatide fixed ratio combination led to a statistically significant improvement in postprandial glycemic control (as shown by the results for 2-hour PPG and glucose excursion after a standard liquid breakfast meal) and in the average of the 7-point SMPG profile. Furthermore the combination had a statistically better effect on body weight compared to insulin glargine.

Overall, the insulin glargine/lixisenatide fixed ratio combination was well tolerated. The safety profile in the combination group was generally consistent with the known safety profile of the GLP-1 receptor agonist class without major differences compared to tile insulin glargine group. Nausea was the most frequently reported adverse event in the combination group. The incidence of symptomatic hypoglycemia (including documented, severe, and probable symptomatic hypoglycemia) was similar in both treatment groups.

In conclusion, the insulin glargine/lixisenatide fixed ratio combination added to metformin for patients not well controlled with this treatment, significantly improved HbA1c and reduced PPG and body weight in comparison to the insulin glargine. The safety profile was consistent with the known effects of GLP-1 receptor agonists, the main AE being nausea.

3 Results 3.1 Study Patients 3.1.1 Patient Accountability

Of the 520 patients screened, 323 (62.1%) patients. were randomized to one of the two treatment groups (161 in the combination group, 162 in the insulin glargine group) in 67 centers distributed among 13 countries (Chile, Czech Republic, Denmark, France, Germany, Hungary, Lithuania, Mexico, Poland, Romania, Slovakia, Sweden, and United States of America). The main reason for screening failure was HbA1c value at screening visit out of the protocol defined range (133 [25.6%] out of 520 screened patients). All 323 randomized patients were exposed to open-label treatment and included in the mITT population for efficacy analyses (Table 1).

TABLE 1

Analysis populations

|  | Insulin Glargine/Lixisenatide Fixed Ratio Combination | Insulin Glargine | All |
|---|---|---|---|
| Randomized population | 161(100%) | 162(100%) | 323(100%) |
| Efficacy population Modified Intent-to-Treat (mITT) | 161 (100%) | 162(100%) | 323(100%) |
| Safety population | 161 | 162 | 323 |

Note:
The safety population patients are tabulated according to treatment actually received (as treated). For the other populations, patients are tabulated according to their randomized treatment. There is no patient randomized in a group and taking another study treatment.

3.1.2 Study Disposition

Table 2 provides the summary of patient disposition for each treatment group.

During the 24-week study treatment period, 11 (6.8%) combination-treated patients prematurely discontinued the IMP, compared with 3 (1.9%) insulin glargine-treated patients. For combination-treated patients, the most common reasons for treatment discontinuation was "adverse event" (6 patients [3.7%] versus 0 patient in the insulin glargine group) followed by "other reasons" (4 patients [2.5%] versus 2 patients [1.2%] in the insulin glargine group).

The time-to-treatment discontinuation due to any reason is depicted in FIG. 1.

TABLE 2

Patient disposition - Randomized population

|  | Insulin Glargine/Lixisenatide Fixed Ratio Combination (N = 161) | Insulin Glargine (N = 162) |
|---|---|---|
| Randomized and treated | 161 (100%) | 162 (100%) |
| Complete the study treatment period | 150 (93.2%) | 159 (98.1%) |
| Did not complete the study treatment period | 11 (6.8%) | 3 (1.9%) |
| Subject's decision for treatment discontinuation | 10 (6.2%) | 3 (1.9%) |
| Reason for treatment discontinuation |  |  |
| Adverse event | 6 (3.7%) | 0 |
| Lack of efficacy | 0 | 0 |
| Poor compliance to protocol | 1 (0.6%) | 1 (0.6%) |
| Lost to follow-up | 0 | 0 |
| Other reasons | 4 (2.5%) | 2 (1.2%) |

Note:
Percentages are calculated using the number of patients randomized as denominator.

3.1.3 Demographics and Baseline Characteristics

Table 3 provides the summary of demographics and patient characteristics at screening or baseline. The demographic and patient characteristics were generally similar between the two treatment groups for the randomized population. The median age was 58 years. The study population was primarily Caucasian (98.5%).

TABLE 3

Demographics and patient characteristics at screening or baseline - Randomized population

|  | Insulin Glargine/Lixisenatide Fixed Ratio Combination (N = 161) | Insulin Glargine (N = 162) | All (N = 323) |
|---|---|---|---|
| Age (years) |  |  |  |
| Number | 161 | 162 | 323 |
| Mean (SD) | 56.9 (9.5) | 56.6 (9.4) | 56.7 (9.4) |
| Median | 58.0 | 57.0 | 58.0 |
| Min:Max | 24:80 | 30:78 | 24:80 |
| Age group (years) [n (%)] |  |  |  |
| Number | 161 | 162 | 323 |
| <50 | 31 (19.3%) | 39 (24.1%) | 70 (21.7%) |
| ≥50 to <65 | 98 (60.9%) | 91 (56.2%) | 189 (58.5%) |
| ≥65 to <75 | 31 (19.3%) | 30 (18.5%) | 61 (18.9%) |
| ≥75 | 1 (0.6%) | 2 (1.2%) | 3 (0.9%) |
| Gender [n (%)] |  |  |  |
| Number | 161 | 162 | 323 |
| Male | 80 (49.7%) | 85 (52.5%) | 165 (51.1%) |
| Female | 81 (50.3%) | 77 (47.5%) | 158 (48.9%) |
| Race [n (%)] |  |  |  |
| Number | 161 | 162 | 323 |
| Caucasian/White | 158 (98.1%) | 160 (98.8%) | 318 (98.5%) |
| Black | 2 (1.2%) | 1 (0.6%) | 3 (0.9%) |
| Asian/Oriental | 1 (0.6%) | (0.6%) | 2 (0.6%) |
| Other | 0 | 0 | 0 |

TABLE 3-continued

Demographics and patient characteristics at screening or baseline - Randomized population

| | Insulin Glargine/Lixisenatide Fixed Ratio Combination (N = 161) | Insulin Glargine (N = 162) | All (N = 323) |
|---|---|---|---|
| Ethnicity [n (%)] | | | |
| Number | 161 | 162 | 323 |
| Hispanic | 35 (21.7%) | 30 (18.5%) | 65 (20.1%) |
| Non Hispanic | 126 (78.3%) | 132 (81.5%) | 258 (79.9%) |
| Screening HbA1c (%) | | | |
| Number | 161 | 162 | 323 |
| Mean (SD) | 8.12 (0.80) | 8.08 (0.77) | 8.10 (0.78) |
| Median | 7.90 | 7.90 | 7.90 |
| Min:Max | 7.0:10.0 | 7.0:9.8 | 7.0:10.0 |
| Randomization strata of Screening HbA1c(%) [n(%)] | | | |
| Number | 161 | 162 | 323 |
| <8% | 81 (50.3%) | 82 (50.6%) | 163 (50.5%) |
| ≥8% | 80 (49.7%) | 80 (49.4%) | 160 (49.5%) |
| Screening BMI (kg/m$^2$) | | | |
| Number | 161 | 162 | 323 |
| Mean (SD) | 32.30 (4.78) | 32.08 (4.27) | 32.19 (4.53) |
| Median | 32.45 | 31.92 | 32.10 |
| Min:Max | 20.5:39.9 | 23.2:40.0 | 20.5:40.0 |
| Randomization strata of Screening BMI (kg/m$^2$) [n(%)] | | | |
| Number | 161 | 162 | 323 |
| <30 | 51 (31.7%) | 51 (31.5%) | 102 (31.6%) |
| ≥30 | 110 (68.3%) | 111 (68.5%) | 221 (68.4%) |
| Baseline BMI (kg/m$^2$) | | | |
| Number | 161 | 162 | 323 |
| Mean (SD) | 32.24 (4.75) | 32.02 (4.35) | 32.13 (4.55) |
| Median | 32.53 | 31.53 | 32.08 |
| Min:Max | 21.0:40.3 | 23.1:41.1 | 21.0:41.1 |
| Baseline BMI categories (kg/m$^2$) [n(%)] | | | |
| Number | 161 | 162 | 323 |
| <30 | 51 (31.7%) | 51 (31.5%) | 102 (31.6%) |
| ≥30 | 110 (68.3%) | 111 (68.5%) | 221 (68.4%) |

BMI = Body Mass Index.

The diabetic history and disease characteristics were generally comparable between the treatment groups, as shown in Table 4. The duration of use and the average daily dose of metformin were similar between the two treatment groups; at baseline, the mean dose was 2084.75 mg for the randomized population. Efficacy variables at baseline were similar across the two treatment groups and are shown in Section 3.2 EFFICACY.

TABLE 4

Disease characteristics at screening or baseline - Randomized population

| | Insulin Glargine/Lixisenatide Fixed Ratio Combination (N = 161) | Insulin Glargine (N = 162) | All (N = 323) |
|---|---|---|---|
| Duration of diabetes (years) | | | |
| Number | 161 | 162 | 323 |
| Mean (SD) | 6.29 (4.29) | 7.10 (5.27) | 6.69 (4.82) |
| Median | 5.42 | 5.35 | 5.35 |
| Min:Max | 1.0:22.4 | 1.0:23.3 | 1.0:23.3 |

TABLE 4-continued

Disease characteristics at screening or baseline - Randomized population

| | Insulin Glargine/Lixisenatide Fixed Ratio Combination (N = 161) | Insulin Glargine (N = 162) | All (N = 323) |
|---|---|---|---|
| Age at onset of Type 2 diabetes (years) | | | |
| Number | 161 | 162 | 323 |
| Mean (SD) | 50.6 (9.6) | 49.4 (9.3) | 50.0 (9.4) |
| Median | 52.0 | 50.0 | 51.0 |
| Min:Max | 20:77 | 25:74 | 20:77 |
| History of gestational diabetes [n(%)] | | | |
| Number (Female) | 81 | 77 | 158 |
| Yes (Female) | 9 (11.1%) | 4 (5.2%) | 13 (8.2%) |
| No (Female) | 72 (88.9%) | 73 (94.8%) | 145 (91.8%) |
| Duration of metformin treatment (years) | | | |
| Number | 161 | 162 | 323 |
| Mean (SD) | 4.10 (3.63) | 4.31 (3.93) | 4.21 (3.78) |
| Median | 3.27 | 3.08 | 3.16 |
| Min:Max | 0.3:20.3 | 0.3:22.1 | 0.3:22.1 |
| Daily dose of metformin at baseline (mg) | | | |
| Number | 161 | 162 | 323 |
| Mean (SD) | 2075.78 (440.71) | 2093.67 (415.51) | 2084.75 (427.68) |
| Median | 2000.00 | 2000.00 | 2000.00 |
| Min:Max | 1500.0:3000.0 | 1500.0:3000.0 | 1500.0:3000.0 |
| Categorized daily dose of metformin at baseline (mg) [n (%)] | | 162 | 323 |
| Number | 161 | 0 | 0 |
| <1500 | 0 | 117 (72.2%) | 229 (70.9%) |
| ≥1500-<2500 | 112 (69.6%) | 32 (19.8%) | 69 (21.4%) |
| ≥2500-<3000 | 37 (23.0%) | 13 (8.0%) | 25 (7.7%) |
| ≥3000 | 12 (7.5%) | | |
| Prior use of GLP-1 receptor agonist [n (%)] | | | |
| Number | 161 | 162 | 323 |
| Yes | 5 (3.1%) | 8 (4.9%) | 13 (4.0%) |
| No | 156 (98.8%) | 154 (94.4%) | 310 (96.0%) |
| Prior use of insulin [n (%)] | | | |
| Number | 161 | 162 | 323 |
| Yes | 2 (1.2%) | 9 (5.6%) | 11 (3.4%) |
| No | 159 (98.8%) | 153 (94.4%) | 312 (96.6%) |
| Diabetic retinopathy [n (%)] | | | |
| Number | 161 | 162 | 323 |
| Yes | 3 (1.9%) | 7 (4.3%) | 10 (3.1%) |
| No | 153 (95.0%) | 149 (92.0%) | 302 (93.5%) |
| Unknown | 5 (3.1%) | 6 (3.7%) | 11 (3.4%) |
| Diabetic sensory or motor neuropathy [n (%)] | | | |
| Number | 161 | 162 | 323 |
| Yes | 26 (16.1%) | 25 (15.4%) | 51 (15.8%) |
| No | 127 (78.9%) | 133 (82.1%) | 260 (80.5%) |
| Unknown | 8 (5.0%) | 4 (2.5%) | 12 (3.7%) |
| Diabetic autonomic neuropathy [n (%)] | | | |
| Number | 161 | 162 | 323 |
| Yes | 1 (0.6%) | 2 (1.2%) | 3 (0.9%) |
| No | 146 (90.7%) | 151 (93.2%) | 297 (92.0%) |
| Unknown | 14 (8.7%) | 9 (5.6%) | 23 (1.7%) |

TABLE 4-continued

Disease characteristics at screening or baseline - Randomized population

| | Insulin Glargine/Lixisenatide Fixed Ratio Combination (N = 161) | Insulin Glargine (N = 162) | All (N = 323) |
|---|---|---|---|
| Diabetic nephropathy [n (%)] | | | |
| Number | 161 | 162 | 323 |
| Yes | 8 (5.0%) | 8 (4.9%) | 16 (5.0%) |
| No | 141 (87.6%) | 148 (91.4%) | 289 (89.5%) |
| Unknown | 12 (7.5%) | 6 (3.7%) | 18 (5.6%) |

GLP = Glucagon like peptide-1.

3.1.4 Dosage and Duration

Treatment exposure and final insulin dose are summarized in Tables 5 and 6. The median duration of treatment exposure was 169.0 days in each treatment group.

TABLE 5

Exposure to investigational product - Safety population

| | Insulin Glargine/Lixisenatide Fixed Ratio Combination (N = 161) | Insulin Glargine (N = 162) |
|---|---|---|
| Cumulative exposure to treatment (patient years) | 71.8 | 74.3 |
| Duration of study treatment (days) | | |
| Number | 161 | 162 |
| Mean (SD) | 162.9 (27.5) | 167.5 (18.2) |
| Median | 169.0 | 169.0 |
| Min:Max | 1:181 | 2:219 |
| Duration of study treatment by category [n (%)] | | |
| Missing duration | 0 | 0 |
| 1-14 days | 2 (1.2%) | 1 (0.6%) |
| 15-28 days | 0 | 1 (0.6%) |
| 29-56 days | 1 (0.6%) | 0 |
| 57-84 days | 3 (1.9%) | 0 |
| 85-168 days | 31 (19.3%) | 42 (25.9%) |
| >168 days | 124 (77.0%) | 118 (72.8%) |
| Missing duration | 0 | 0 |
| ≥1 day | 161 (100%) | 162 (100%) |
| ≥15 days | 159 (98.8%) | 161 (99.4%) |
| ≥29 days | 159 (98.8%) | 160 (98.8%) |
| ≥57 days | 158 (98.1%) | 160 (98.8%) |
| ≥85 days | 155 (96.3%) | 160 (98.8%) |
| ≥169 days | 124 (77.0%) | 118 (72.8%) |

Note:
Patients are considered in the treatment group they actually received at randomization. Duration of exposure = (date of the last open-label IMP injection – date of the first open-label IMP injection) + 1.

In the combination group the final daily dose at the end of the treatment period was >20 U/10 μg and ≤40 U/20 μg for 70 (43.5%) patients and >40 U/20 μg and ≤60 U/30 μg for 68 (42.2%) patients. More patients (23 [14.3%]) in the combination group than in the insulin glargine group (16 [9.9%]) had a final daily dose in the category of ≤20 U. More patients in the insulin glargine group (27 [16.7%]) had a final daily dose >60 U compared to the combination group (0 patient as required by the protocol).

TABLE 6

Number (%) of patients by final insulin dose at the end of the open-label treatment - Safety population

| Final Insulin dose | Insulin Glargine/Lixisenatide Fixed Ratio Combination (N = 161) | Insulin Glargine (N = 162) |
|---|---|---|
| ≤20 U | 23 (14.3%) | 16 (9.9%) |
| >20 U to ≤40 U | 70 (43.5%) | 73 (45.1%) |
| >40 U to ≤60 U | 68 (42.2%) | 46 (28.4%) |
| >60 U | 0 | 27 (16.7%) |

Note:
Percentages are calculated using the number of safety patients as the denominator.

3.2 Efficacy

3.2.1 Primary Efficacy Endpoint

Main Analysis

Table 7 summarizes the results of the primary efficacy endpoint, change from baseline to Week 24 in HbA1c using an ANCOVA analysis with missing data imputed using the last observation carried forward (LOCF) approach. The least squared (LS) mean changes from baseline to Week 24 in HbA1c were −1.82% for the combination group and −1.64% for the insulin glargine group (LS mean difference vs insulin glargine=−0.17%, 95% CI: −0.312% to −0.037%). Based on the pre-specified primary analysis, the non-inferiority of the combination group compared to the insulin glargine group was demonstrated, as the upper bound of the two-sided 95% CI of the LS mean difference was less than the predefined non-inferiority margin of 0.4%. Statistical superiority of the combination over insulin glargine was also demonstrated (LS mean difference vs. insulin glargine=−0.17%, p-value=0.0130).

Figure 2:
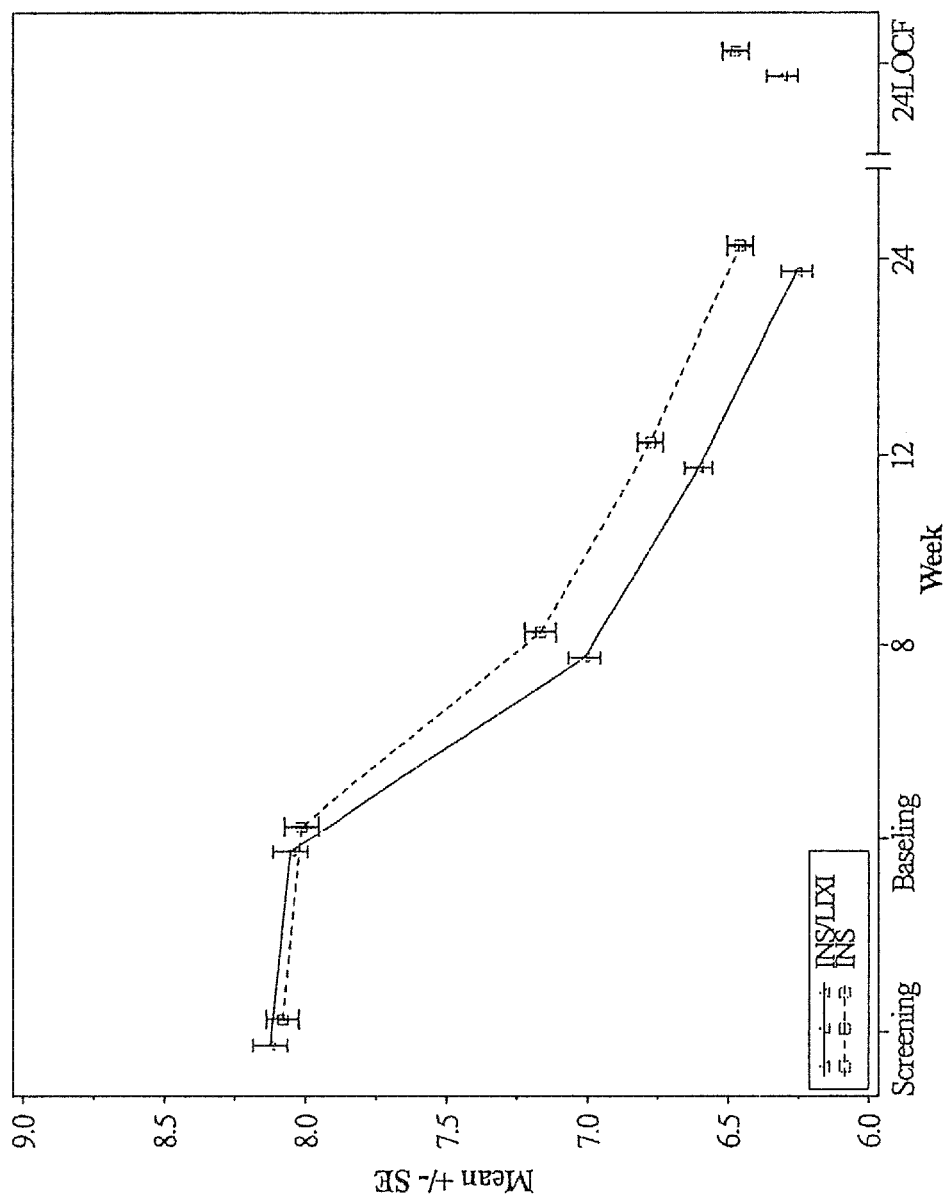
FIG. 2—Plot of mean HbA1c (%) by visit—mITT population. LOCF=Last observation carried forward. Note: The plot included measurements obtained before the introduction of rescue medication and up to 14 days after the last injection of the investigational medicinal product. INS/LIXI=Insulin Glargine/Lixisenatide Fixed Ratio Combination, INS=Insulin Glargine.

FIG. 2 illustrates the Mean (±SE) in HbA1c over time during the 24-week treatment period. In both treatment groups, the largest decrease in HbA1c mean was observed at Week 24.

TABLE 7

Mean change in HbA1c (%) from baseline to Week 24 - mITT population

| HbA1c (%) | Insulin Glargine/Lixisenatide Fixed Ratio Combination (N = 161) | Insulin Glargine (N = 162) |
|---|---|---|
| Baseline | | |
| Number | 160 | 161 |
| Mean (SD) | 8.06 (0.79) | 8.01 (0.81) |
| Median | 7.90 | 7.80 |
| Min:Max | 6.3:10.2 | 6.7:10.0 |
| Week 24 (LOCF) | | |
| Number | 160 | 161 |
| Mean (SD) | 6.31 (0.72) | 6.47 (0.64) |
| Median | 6.15 | 6.40 |
| Min:Max | 5.1:9.1 | 5.1:8.7 |
| Change from baseline to Week 24 (LOCF) | | |
| Number | 160 | 161 |
| Mean (SD) | −1.76 (0.84) | −1.54 (0.87) |
| Median | −1.60 | −1.40 |
| Min:Max | −4.3:0.4 | −3.7:0.9 |
| LS Mean (SE)[a] | −1.82 (0.058) | −1.64 (0.057) |
| LS Mean difference (SE) vs. insulin glargine[a] | −0.17 (0.070) | |
| 95% CI | (−0.312 to −0.037) | |
| p-value | 0.0130 | |

LOCF = Last observation carried forward.
[a]Analysis of covariance (ANCOVA) model with treatment groups (insulin glargine/lixisenatide fixed dose combination, insulin glargine), randomization strata of screening HbA1c (<8.0%, ≥8.0%), randomization strata of screening BMI (<30, ≥30 kg/m$^2$), and country as fixed effects and baseline HbA1c value as a covariate.
The analysis included measurements obtained before the introduction of rescue medication and up to 14 days after the last injection of the investigational medicinal product.
Patients with both baseline and Week 24 (LOCF) measurements are included.

Table 8 provides the proportion of responders with HbA1c ≤6.5% or <7% at Week 24, respectively. Although the between-group differences were not statistically significant as shown by the 95% CI of proportion difference, a higher percentage of patients in the combination group reached target HbA1c ≤6.5% (71.9% versus 64.6%) or <7% (84.4% versus 78.3%) as compared with the insulin glargine group.

TABLE 8

Number (%) of patients with HbA1c value ≤6.5% or <7% respectively at Week 24 - mITT population

| HbA1c (%) | Insulin Glargine/Lixisenatide Fixed Ratio Combination (N = 161) | Insulin Glargine (N = 162) |
|---|---|---|
| Number | 160 | 161 |
| ≤6.5% | 115 (71.9%) | 104 (64.6%) |
| Proportion difference (95% CI) vs. insulin glargine[a] | 7.3% (−2.63% to 17.28%) | — |

TABLE 8-continued

Number (%) of patients with HbA1c value ≤6.5% or <7% respectively at Week 24 - mITT population

| HbA1c (%) | Insulin Glargine/Lixisenatide Fixed Ratio Combination (N = 161) | Insulin Glargine (N = 162) |
|---|---|---|
| Number | 160 | 161 |
| <7.0% | 135 (84.4%) | 126 (78.3%) |
| Proportion difference (95% CI) vs. insulin glargine[a] | 6.2% (−2.16% to 14.47%) | — |

[a]Weighted average of proportion difference between treatment groups (insulin glargine/lixisenatide fixed dose combination, insulin glargine) from each strata (randomization strata of screening HbA1c [<8.0, ≥8.0%], randomization strata of screening BMI [<30 or ≥30 kg/m$^2$]) using Cochran-Mantel-Haenszel (CMH) weights.
Proportion difference = difference of the proportions of patients achieving HbA1c value ≤6.5% or <7% respectively.
The analysis included measurements obtained before the introduction of rescue medication and up to 14 days after the last injection of the investigational medicinal product.

3.2.2 Other Key Efficacy Endpoints

Figure 3:
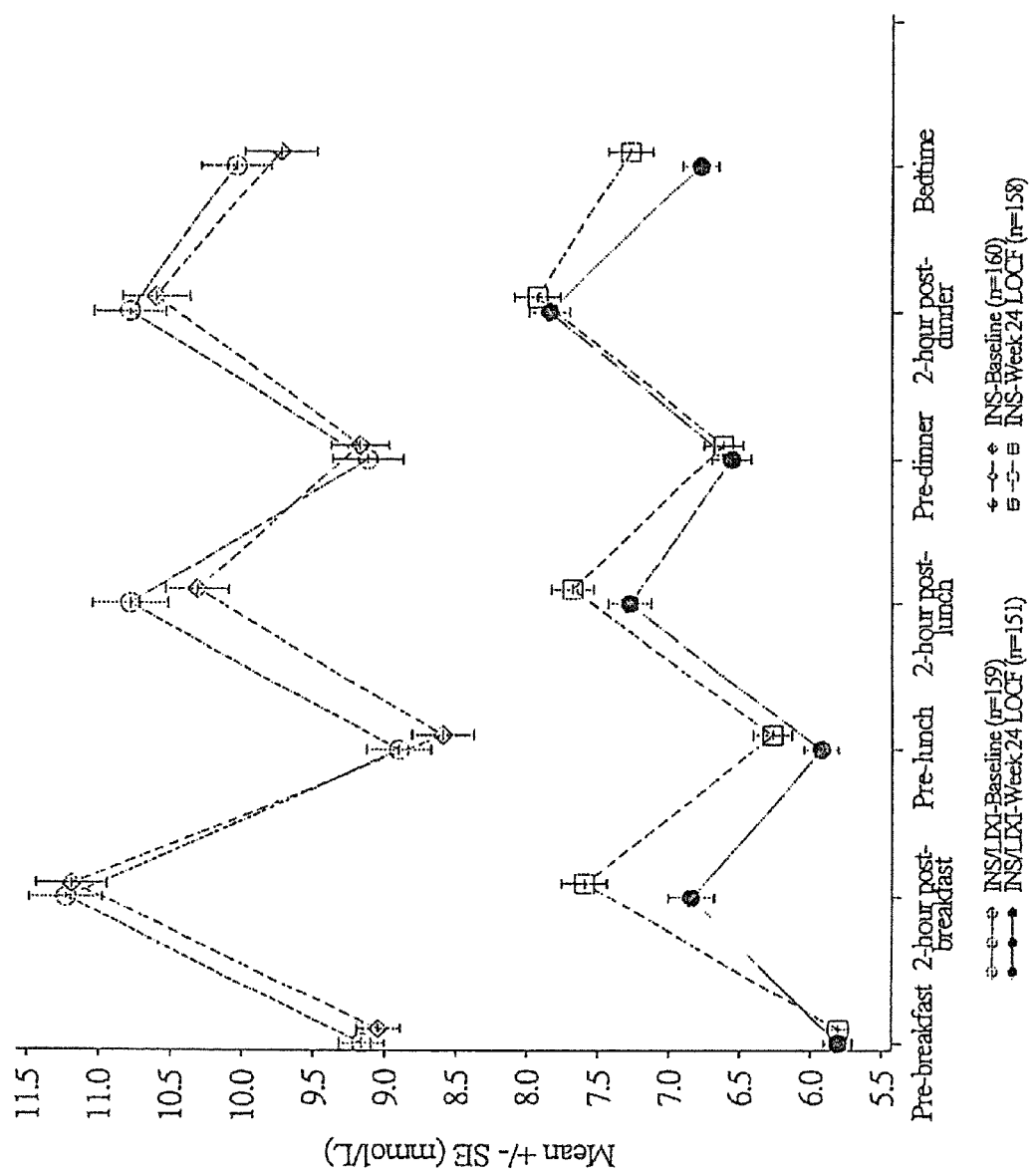
FIG. 3—Plot of mean 7-point Self Monitored Plasma Glucose (SMPG) profiles (mmol/L) at baseline and Week 24 (LOCF)—mITT population. LOCF=Last observation carried forward. The analysis included measurements obtained before the introduction of rescue medication and up to the date of last injection of the investigational medicinal product. INS/LIXI=Insulin Glargine/Lixisenatide Fixed Ratio Combination, INS=Insulin Glargine.
Figure 4:
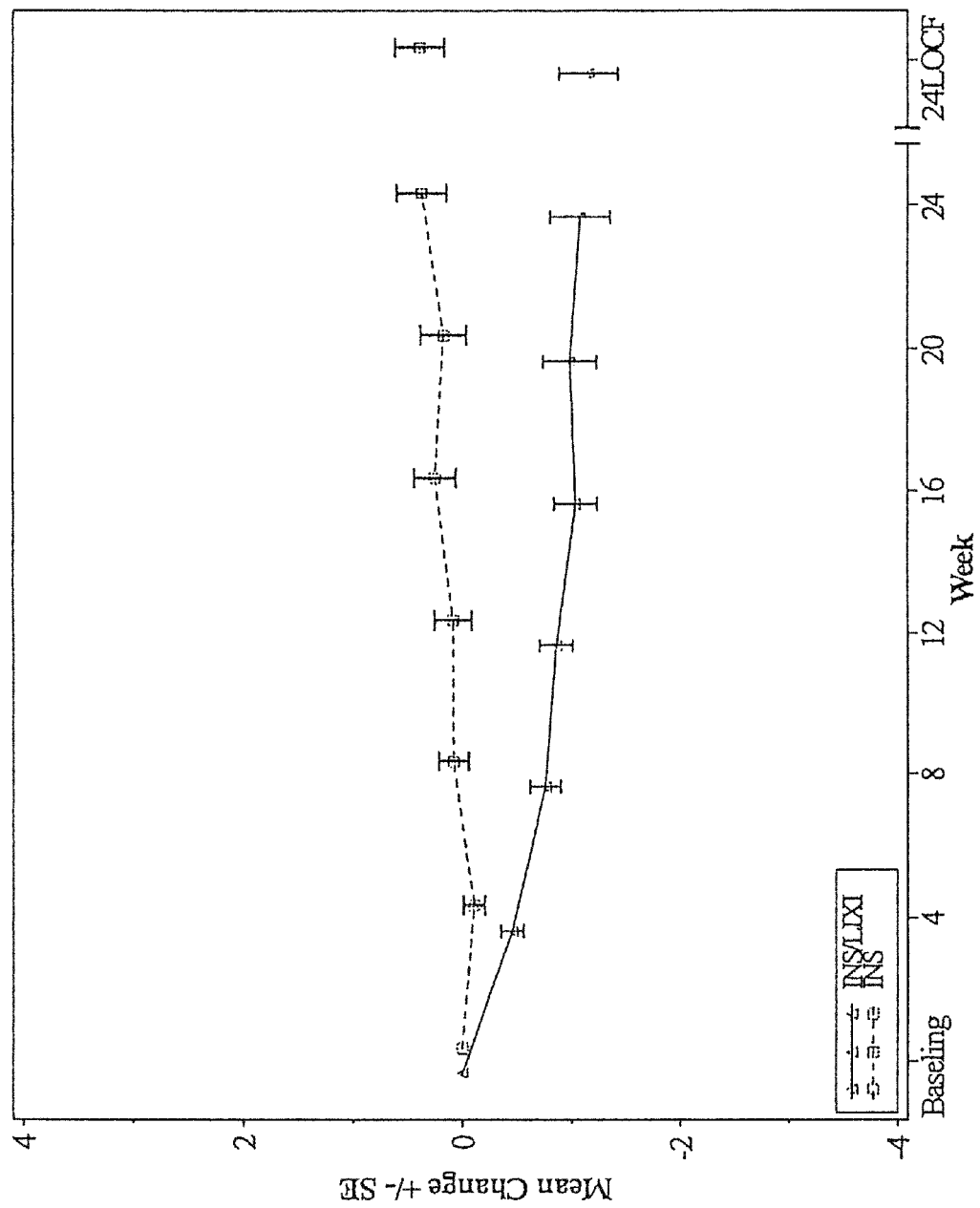
FIG. 4—Plot of mean change in body weight (kg) from baseline by visit—mITT population. LOCF=Last observation carried forward. The analysis included measurements obtained before the introduction of rescue medication and up to 3 days after the last injection of the investigational medicinal product. INS/LIXI=Insulin Glargine/Lixisenatide Fixed Ratio Combination, INS=Insulin Glargine.
Figure 5:
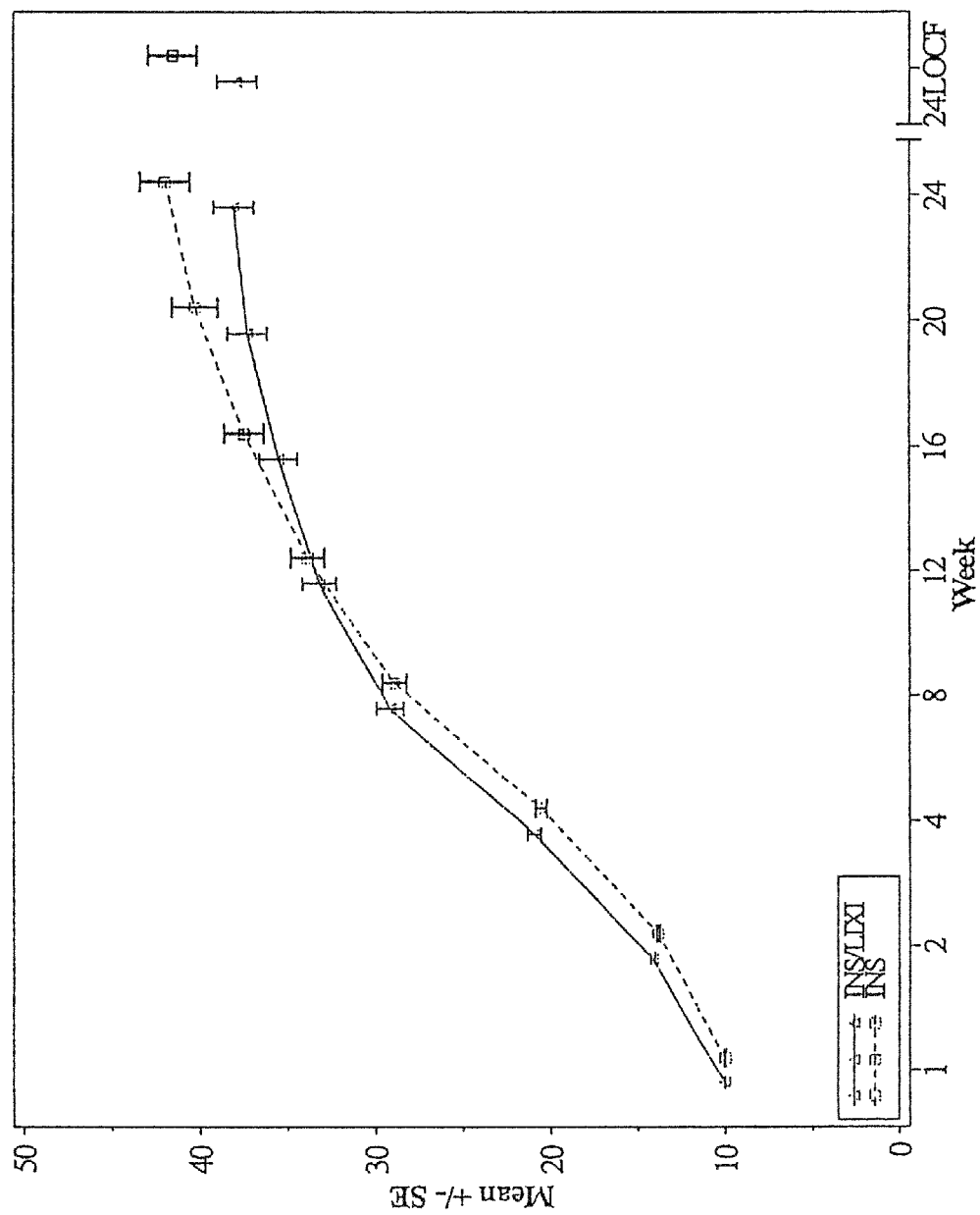
FIG. 5—Plot of mean average daily insulin glargine dose (U) by visit—mITT population. LOCF=Last observation carried forward. The analysis included measurements obtained before the introduction of rescue medication and up to the date of last injection of the investigational medicinal product. INS/LIXI=Insulin Glargine/Lixisenatide Fixed Ratio Combination, INS=Insulin Glargine.

Table 9 to Table 14 summarize the ANCOVA analyses of 2-hour PPG, PG excursion, average 7-point SMPG profile, body weight, average insulin daily dose, and FPG, respectively. FIGS. 3 to 5 illustrate average 7-point SMPG profile, body weight, and average insulin daily dose over time during the treatment period.

Treatment with the combination significantly improved postprandial glycemic control in comparison to insulin glargine as shown by the results for the 2-hour PPG and PG excursion. For 2-hour PPG (Table 9), the LS mean change from baseline to Week 24 was −7.49 mmol/L for the combination group and −4.33 mmol/L for the insulin glargine group (LS mean difference vs insulin glargine=−3.17 mmol/L; p-value <0.0001). For 2-hour PG excursion (Table 10), the LS mean change from baseline to Week 24 was −3.91 mmol/L for the combination group and −0.67 mmol/L for the insulin glargine group (LS mean difference versus insulin glargine=−3.24 mmol/L; p-value <0.0001).

TABLE 9

Mean change in 2-hour postprandial plasma glucose (mmol/L) from baseline to Week 24 - mITT

| 2-hour postprandial plasma glucose (mmol/L) | Insulin Glargine/Lixisenatide Fixed Ratio Combination (N = 161) | Insulin Glargine (N = 162) |
|---|---|---|
| Baseline | | |
| Number | 151 | 153 |
| Mean (SD) | 16.08 (3.62) | 15.51 (3.88) |
| Median | 15.90 | 15.40 |
| Min:Max | 7.8:26.6 | 5.6:24.8 |
| Week 24 (LOCF) | | |
| Number | 151 | 153 |
| Mean (SD) | 8.51 (3.23) | 11.55 (2.83) |
| Median | 7.80 | 11.10 |
| Min:Max | 3.4:19.7 | 3.5:20.3 |
| Change from baseline to Week 24 (LOCF) | | |
| Number | 151 | 153 |
| Mean (SD) | −7.56 (4.34) | −3.96 (4.05) |
| Median | −7.50 | −3.90 |
| Min:Max | −18.2:5.1 | −14.9:14.1 |
| LS Mean (SE)[a] | −7.49 (0.283) | −4.33 (0.274) |
| LS Mean difference (SE) vs. insulin glargine[a] | −3.17 (0.337) | |

TABLE 9-continued

Mean change in 2-hour postprandial plasma glucose (mmol/L)
from baseline to Week 24 - mITT

| 2-hour postprandial plasma glucose (mmol/L) | Insulin Glargine/Lixisenatide Fixed Ratio Combination (N = 161) | Insulin Glargine (N = 162) |
|---|---|---|
| 95% CI | (−3.832 to −2.504) | |
| p-value | <.0001 | |

LOCF = Last observation carried forward.

[a]Analysis of covariance (ANCOVA) model with treatment groups (insulin glargine/lixisenatide fixed dose combination, insulin glargine), randomization strata of screening HbA1c (<8.0%, ≥8.0%), randomization strata of screening BMI (<30, ≥30 kg/m$^2$), and country as fixed effects and baseline 2-hour postprandial plasma glucose value as a covariate.
The analysis included measurements obtained before the introduction of rescue medication and up to the date of the last injection of the investigational medicinal product.
Patients with both baseline and Week 24 (LOCF) measurements are included.

TABLE 10

Mean change in 2-hour plasma glucose excursion (mmol/L) from baseline to Week 24 - mITT population

| 2-hour postprandial plasma glucose (mmol/L) | Insulin Glargine/Lixisenatide Fixed Ratio Combination (N = 161) | Insulin Glargine (N = 162) |
|---|---|---|
| Baseline | | |
| Number | 151 | 152 |
| Mean (SD) | 6.04 (2.67) | 5.94 (2.95) |
| Median | 5.90 | 5.80 |
| Min:Max | −3.1:13.6 | −4.3:13.3 |
| Week 24 (LOCF) | | |
| Number | 151 | 152 |
| Mean (SD) | 2.15 (3.18) | 5.33 (2.79) |
| Median | 1.90 | 5.05 |
| Min:Max | −7.1:12.8 | −3.4:11.1 |
| Change from baseline to Week 24 (LOCF) | | |
| Number | 151 | 152 |
| Mean (SD) | −3.89 (3.75) | −0.61 (3.03) |
| Median | −3.70 | −0.75 |
| Min:Max | −13.2:7.5 | −7.6:13.7 |
| LS Mean (SE)[a] | −3.91 (0.277) | −0.67 (0.269) |
| LS Mean difference (SE) vs. insulin glargine[a] | −3.24 (0.331) | |
| 95% CI | (−3.895 to −2.592) | |
| p-value | <.0001 | |

LOCF = Last observation carried forward.

[a]Analysis of covariance (ANCOVA) model with treatment groups (insulin glargine/lixisenatide fixed dose combination, insulin glargine), randomization strata of screening HbA1c (<8.0%, ≥8.0%), randomization strata of screening BMI (<30, ≥30 kg/m$^2$), and country as fixed effects and baseline 2-hour postprandial plasma glucose value as a covariate.
The analysis included measurements obtained before the introduction of rescue medication and up to the date of the last injection of the investigational medicinal product.
Patients with both baseline and Week 24 (LOCF) measurements are included.

For the average 7-point SMPG (Table 11), the combination-treated patients had a statistically significant greater reduction compared to the insulin glargine-treated patients (LS mean difference of −0.30 mmol/L; p-value=0.0154). FIG. 3 illustrates the 7-point SMPG for each timepoint at baseline and week 24 (LOCF).

TABLE 11

Mean change in average 7-point Self Monitored Plasma Glucose (SMPG) profiles (mmol/L) from baseline to Week 24 - mITT population

| Average 7-point Self Monitored Plasma Glucose (SMPG) (mmol/L) | Insulin Glargine/Lixisenatide Fixed Ratio Combination (N = 161) | Insulin Glargine (N = 162) |
|---|---|---|
| Baseline | | |
| Number | 149 | 155 |
| Mean (SD) | 10.01 (2.49) | 9.82 (2.10) |
| Median | 9.56 | 9.47 |
| Min:Max | 6.0:24.2 | 5.7:17.3 |
| Week 24 (LOCF) | | |
| Number | 149 | 155 |
| Mean (SD) | 6.74 (1.12) | 7.01 (1.15) |
| Median | 6.57 | 6.94 |
| Min:Max | 4.7:11.4 | 4.8:10.6 |
| Change from baseline to Week 24 (LOCF) | | |
| Number | 149 | 155 |
| Mean (SD) | −3.27 (2.59) | −2.81 (2.18) |
| Median | −2.80 | −2.31 |
| Min:Max | −17.4:2.3 | −12.0:0.8 |
| LS Mean (SE)[a] | −3.23 (0.104) | −2.93 (0.101) |
| LS Mean difference (SE) vs. insulin glargine[a] | −0.30 (0.125) | |
| 95% CI | (−0.550 to −0.058) | |
| p-value | 0.0154 | |

LOCF = Last observation carried forward.

[a]Analysis of covariance (ANCOVA) model with treatment groups (insulin glargine/lixisenatide fixed dose combination, insulin glargine), randomization strata of screening HbA1c (<8.0%, ≥8.0%), randomization strata of screening BMI (<30, ≥30 kg/m$^2$), and country as fixed effects and baseline 2-hour postprandial plasma glucose value as a covariate.
The analysis included measurements obtained before the introduction of rescue medication and up to the date of the last injection of the investigational medicinal product.
Patients with both baseline and Week 24 (LOCF) measurements are included.

The LS mean body weight decreased from baseline to week 24 by 0.97 kg for the combination-treated patients and increased by 0.48 kg for the insulin glargine-treated patients (LS mean difference versus insulin glargine=−1.44 kg) with statistically significant difference observed between treatment groups (p-value <0.0001) (Table 12).

TABLE 12

Mean change in body weight (kg) from baseline to Week 24 - mITT population

| Body weight (kg) | Insulin Glargine/Lixisenatide Fixed Ratio Combination (N = 161) | Insulin Glargine (N = 162) |
|---|---|---|
| Baseline | | |
| Number | 159 | 160 |
| Mean (SD) | 90.26 (17.63) | 91.70 (16.62) |
| Median | 90.60 | 91.20 |
| Min:Max | 45.7:138.0 | 54.2:173.6 |
| Week 24 (LOCF) | | |
| Number | 159 | 160 |
| Mean (SD) | 89.10 (16.89) | 92.09 (16.30) |
| Median | 90.60 | 91.00 |
| Min:Max | 44.1:129.0 | 56.3:173.4 |
| Change from baseline to Week 24 (LOCF) | | |
| Number | 159 | 160 |
| Mean (SD) | −1.16 (3.45) | 0.39 (2.96) |
| Median | −1.00 | 0.35 |
| Min:Max | −12.0:7.2 | −10.0:8.2 |

TABLE 12-continued

Mean change in body weight (kg) from baseline to Week 24 - mITT population

| Body weight (kg) | Insulin Glargine/Lixisenatide Fixed Ratio Combination (N = 161) | Insulin Glargine (N = 162) |
|---|---|---|
| LS Mean (SE)[a] | −0.97 (0.289) | 0.48 (0.282) |
| LS Mean difference (SE) vs. insulin glargine[a] | −1.44 (0.340) | |
| 95% CI | (−2.110 to −0.773) | |
| p-value | <.0001 | |

LOCF = Last observation carried forward.

[a]Analysis of covariance (ANCOVA) model with treatment groups (insulin glargine/lixisenatide fixed dose combination, insulin glargine), randomization strata of screening HbA1c (<8.0%, ≥8.0%), randomization strata of screening BMI (<30, ≥30 kg/m²), and country as fixed effects and baseline 2-hour postprandial plasma glucose value as a covariate.

The analysis included measurements obtained before the introduction of rescue medication and up to the date of the last injection of the investigational medicinal product.

Patients with both baseline and Week 24 (LOCF) measurements are included.

The LS mean in average insulin glargine daily dose at Week 24 was 36.08 U for the combination group and 39.32 U for the insulin glargine group, and the difference between the treatment groups was borderline significant (LS mean difference vs insulin glargine=−3.24 U; p-value=0.0583) (Table 13).

TABLE 13

Average daily insulin glargine dose (U) at Week 24 - mITT population

| Average daily insulin glargine dose (U) | Insulin Glargine/Lixisenatide Fixed Ratio Combination (N = 161) | Insulin Glargine (N = 162) |
|---|---|---|
| Week 24 (LOCF) | | |
| Number | 161 | 162 |
| Mean (SD) | 37.90 (14.56) | 41.54 (18.37) |
| Median | 38.00 | 38.00 |
| Min:Max | 10.0:64.0 | 10.0:98.6 |
| | | 39.32 (1.384) |
| LS Mean difference (SE) vs. insulin glargine[a] | 36.08 (1.415) −3.24 (1.704) | |
| 95% CI | (−6.592 to 0.114) | |
| p-value | 0.0583 | |

LOCF = Last observation carried forward.

[a]Analysis of covariance (ANCOVA) model with treatment groups (insulin glargine/lixisenatide fixed dose combination, insulin glargine), randomization strata of screening HbA1c (<8.0%, ≥8.0%), randomization strata of screening BMI (<30, ≥30 kg/m²), and country as fixed effects.

The analysis included measurements obtained before the introduction of rescue medication and up to the date of the last injection of the investigational medicinal product.

Similar reduction in mean change FPG from baseline to Week 24 (LS mean: −3.35 mmol/L in the combination group; −3.51 mmol/L in insulin glargine group) was observed.

Only one patient in the insulin glargine group required rescue therapy during the 24 weeks treatment period.

TABLE 14

Mean change in fasting plasma glucose (mmol/L) from baseline to Week 24 - mITT population

| Fasting plasma glucose (mmol/L) | Insulin Glargine/Lixisenatide Fixed Ratio Combination (N = 161) | Insulin Glargine (N = 162) |
|---|---|---|
| Baseline | | |
| Number | 159 | 160 |
| Mean (SD) | 9.79 (2.19) | 9.48 (2.16) |
| Median | 9.40 | 9.10 |
| Min:Max | 6.2:23.0 | 3.8:18.4 |
| Week 24 (LOCF) | | |
| Number | 159 | 160 |
| Mean (SD) | 6.39 (1.58) | 6.20 (1.35) |
| Median | 6.20 | 5.95 |
| Min:Max | 4.2:15.1 | 3.1:10.9 |
| Change from baseline to Week 24 (LOCF) | | |
| Number | 159 | 160 |
| Mean (SD) | −3.40 (2.09) | −3.28 (2.39) |
| Median | −3.30 | −3.00 |
| Min:Max | −14.9:2.8 | −13.6:4.4 |
| LS Mean (SE)[a] | −3.35 (0.130) | −3.51 (0.128) |
| LS Mean difference (SE) vs. insulin glargine[a] | 0.16 (0.156) | |
| 95% CI | (−0.143 to 0.471) | |
| p-value | 0.2940 | |

LOCF = Last observation carried forward.

[a]Analysis of covariance (ANCOVA) model with treatment groups (insulin glargine/lixisenatide fixed dose combination, insulin glargine), randomization strata of screening HbA1c (<8.0%, ≥8.0%), randomization strata of screening BMI (<30, ≥30 kg/m²), and country as fixed effects and baseline fasting plasma glucose as a covariate.

The analysis included measurements obtained before the introduction of rescue medication and up to the date of the last injection of the investigational medicinal product.

Patients with both baseline and Week 24 (LOCF) measurements are included.

3.3 Safety

Symptomatic hypoglycemia events were documented on a specific hypoglycemia event form, and not an AE CRF page, and thus were not included in the TEAE summaries. They are summarized separately from TEAEs (see Section 3.3.5).

3.3.1 Treatment-Emergent Adverse Events

Table 15 presents the overall summary of patients who had adverse events during the 24-week open-label treatment period. Slightly more patients reported TEAEs in the combination group (86 [53.4%]) than in the insulin glargine group (82 [50.6%]), which is mainly attributable to the difference in gastrointestinal disorders SOC events (25 [15.5%] in the combination group vs 15 [9.3%] in the insulin glargine group). As shown in Table 16, the most frequently reported TEAE in the combination group was nausea (12 [7.5%] versus 0 in the insulin glargine group), and in the insulin glargine group was headache (12 [7.4%] versus 8 [5.0%] in the combination group).

TABLE 15

Overview of adverse event profile: treatment emergent adverse events - Safety population

|  | Insulin Glargine/Lixisenatide Fixed Ratio Combination (N = 161) | Insulin Glargine (N = 162) |
| --- | --- | --- |
| Patients with any TEAE | 86 (53.4%) | 82 (50.6%) |
| Patients with any treatment emergent SAE | 9 (5.6%) | 6 (3.7%) |
| Patients with any TEAE leading to death | 0 | 0 |
| Patients with any TEAE leading to permanent treatment discontinuation | 6 (3.7%) | 0 |

TEAE: Treatment emergent adverse event,
SAE: Serious adverse event.
n (%) = number and percentage of patients with at least one TEAE.

TABLE 16

Number (%) of patients with TEAE(s) that occurred with PT >=1% in any treatment group by primary SOC, HLGT, HLT and PT - Safety population

| PRIMARY SYSTEM ORGAN CLASS<br>HLGT: High Level Group Term<br>HLT: High Level Term<br>Preferred Term n (%) | Insulin Glargine/Lixisenatide Fixed Ratio Combination (N = 161) | Insulin Glargine (N = 162) |
| --- | --- | --- |
| Any TEAE | 86 (53.4%) | 82 (50.6%) |
| Infections and infestations | 33 (20.5%) | 38 (23.5%) |
| HLGT: Infections - pathogen unspecified | 27 (16.8%) | 31 (19.1%) |
| HLT: Abdominal and gastrointestinal infections | 5 (3.1%) | 1 (0.6%) |
| Gastroenteritis | 5 (3.1%) | 1 (0.6%) |
| HLT: Dental and oral soft tissue infections | 0 | 3 (1.9%) |
| Tooth abscess | 0 | 2 (1.2%) |
| HLT: Lower respiratory tract and lung infections | 3 (1.9%) | 1 (0.6%) |
| Bronchitis | 3 (1.9%) | 1 (0.6%) |
| HLT: Upper respiratory tract infections | 15 (9.3%) | 21 (13.0%) |
| Nasopharyngitis | 9 (5.6%) | 9 (5.6%) |
| Rhinitis | 2 (1.2%) | 2 (1.2%) |
| Sinusitis | 0 | 3 (1.9%) |
| Upper respiratory tract infection | 3 (1.9%) | 5 (3.1%) |
| HLT: Urinary tract infections | 4 (2.5%) | 3 (1.9%) |
| Cystitis | 2 (1.2%) | 2 (1.2%) |
| Urinary tract infection | 2 (1.2%) | 1 (0.6%) |
| HLGT: Viral infectious disorders | 6 (3.7%) | 8 (4.9%) |
| HLT: Influenza viral infections | 4 (2.5%) | 6 (3.7%) |
| Influenza | 4 (2.5%) | 6 (3.7%) |
| Metabolism and nutrition disorders | 6 (3.7%) | 1 (0.6%) |
| HLGT: Appetite and general nutritional disorders | 2 (1.2%) | 1 (0.6%) |
| HLT: Appetite disorders | 2 (1.2%) | 1 (0.6%) |
| Decreased appetite | 2 (1.2%) | 0 |
| HLGT: Lipid metabolism disorders | 4 (2.5%) | 0 |
| HLT: Elevated triglycerides | 2 (1.2%) | 0 |
| Hypertriglyceridaemia | 2 (1.2%) | 0 |
| Psychiatric disorders | 6 (3.7%) | 2 (1.2%) |
| HLGT: Depressed mood disorders and disturbances | 0 | 2 (1.2%) |
| HLT: Depressive disorders | 0 | 2 (1.2%) |
| Depression | 0 | 2 (1.2%) |
| HLGT: Sleep disorders and disturbances | 4 (2.5%) | 0 |
| HLT: Disturbances in initiating and maintaining sleep | 3 (1.9%) | 0 |
| Insomnia | 3 (1.9%) | 0 |
| Nervous system disorders | 19 (11.8%) | 20 (12.3%) |
| HLGT: Headaches | 9 (5.6%) | 13 (8.0%) |
| HLT: Headaches NEC | 8 (5.0%) | 12 (7.4%) |
| Headache | 8 (5.0%) | 12 (7.4%) |
| HLGT: Neurological disorders NEC | 7 (4.3%) | 5 (3.1%) |
| HLT: Neurological signs and symptoms NEC | 3 (1.9%) | 3 (1.9%) |
| Dizziness | 3 (1.9%) | 1 (0.6%) |
| Presyncope | 0 | 2 (1.2%) |
| HLGT: Peripheral neuropathies | 2 (1.2%) | 2 (1.2%) |
| HLT: Chronic polyneuropathies | 2 (1.2%) | 2 (1.2%) |
| Diabetic neuropathy | 2 (1.2%) | 2 (1.2%) |
| HLGT: Spinal cord and nerve root disorders | 2 (1.2%) | 2 (1.2%) |
| HLT: Lumbar spinal cord and nerve root disorders | 2 (1.2%) | 2 (1.2%) |
| Sciatica | 2 (1.2%) | 2 (1.2%) |
| Eye disorders | 4 (2.5%) | 7 (4.3%) |

TABLE 16-continued

Number (%) of patients with TEAE(s) that occurred with PT >=1% in any treatment group by primary SOC, HLGT, HLT and PT - Safety population

| PRIMARY SYSTEM ORGAN CLASS<br>HLGT: High Level Group Term<br>HLT: High Level Term<br>Preferred Term n (%) | Insulin Glargine/Lixisenatide Fixed Ratio Combination (N = 161) | Insulin Glargine (N = 162) |
|---|---|---|
| HLGT: Ocular infections, irritations and inflammations | 3 (1.9%) | 4 (2.5%) |
| HLT: Conjunctival infections, irritations and inflammations | 3 (1.9%) | 2 (1.2%) |
| Conjunctivitis | 2 (1.2%) | 2 (1.2%) |
| Ear and labyrinth disorders | 0 | 2 (1.2%) |
| HLGT: Inner ear and VIIIth cranial nerve disorders | 0 | 2 (1.2%) |
| HLT: Inner ear signs and symptoms | 0 | 2 (1.2%) |
| Tinnitus | 0 | 2 (1.2%) |
| Cardiac disorders | 4 (2.5%) | 1 (0.6%) |
| HLGT: Cardiac arrhythmias | 2 (1.2%) | 1 (0.6%) |
| HLT: Supraventricular arrhythmias | 2 (1.2%) | 1 (0.6%) |
| Atrial fibrillation | 2 (1.2%) | 1 (0.6%) |
| Vascular disorders | 3 (1.9%) | 3 (1.9%) |
| HLGT: Vascular hypertensive disorders | 1 (0.6%) | 2 (1.2%) |
| HLT: Vascular hypertensive disorders NEC | 1 (0.6%) | 2 (1.2%) |
| Hypertension | 1 (0.6%) | 2 (1.2%) |
| Respiratory, thoracic and mediastinal disorders | 6 (3.7%) | 4 (2.5%) |
| HLGT: Respiratory disorders NEC | 3 (1.9%) | 2 (1.2%) |
| HLT: Coughing and associated symptoms | 2 (1.2%) | 0 |
| Cough | 2 (1.2%) | 0 |
| Gastrointestinal disorders | 25 (15.5%) | 15 (9.3%) |
| HLGT: Gastrointestinal motility and defaecation conditions | 8 (5.0%) | 7 (4.3%) |
| HLT: Diarrhoea (excl infective) | 5 (3.1%) | 6 (3.7%) |
| Diarrhoea | 5 (3.1%) | 6 (3.7%) |
| HLT: Gastrointestinal atonic and hypomotility disorders NEC | 4 (2.5%) | 1 (0.6%) |
| Constipation | 3 (1.9%) | 0 |
| HLGT: Gastrointestinal signs and symptoms | 18 (11.2%) | 7 (4.3%) |
| HLT: Dyspeptic signs and symptoms | 2 (1.2%) | 1 (0.6%) |
| Dyspepsia | 2 (1.2%) | 1 (0.6%) |
| HLT: Flatulence, bloating and distension | 1 (0.6%) | 2 (1.2%) |
| Abdominal distension | 1 (0.6%) | 2 (1.2%) |
| HLT: Nausea and vomiting symptoms | 14 (8.7%) | 1 (0.6%) |
| Nausea | 12 (7.5%) | 0 |
| Vomiting | 4 (2.5%) | 1 (0.6%) |
| Musculoskeletal and connective tissue disorders | 21 (13.0%) | 13 (8.0%) |
| HLGT: Joint disorders | 6 (3.7%) | 6 (3.7%) |
| HLT: Joint related signs and symptoms | 4 (2.5%) | 3 (1.9%) |
| Arthralgia | 4 (2.5%) | 3 (1.9%) |
| HLT: Osteoarthropathies | 1 (0.6%) | 2 (1.2%) |
| Osteoarthritis | 1 (0.6%) | 2 (1.2%) |
| HLGT: Musculoskeletal and connective tissue deformities (incl intervertebral disc disorders | 3 (1.9%) | 2 (1.2%) |
| HLT: Intervertebral disc disorders NEC | 2 (1.2%) | 2 (1.2%) |
| Intervertebral disc disorder | 1 (0.6%) | 2 (1.2%) |
| HLGT: Musculoskeletal and connective tissue disorders NEC | 10 (6.2%) | 3 (1.9%) |
| HLT: Musculoskeletal and connective tissue pain and discomfort | 10 (6.2%) | 3 (1.9%) |
| Back pain Musculoskeletal pain 2 (1.2%) 1 (0.6%) | 5 (3.1%) | 2 (1.2%) |
| Pain in extremity | 6 (3.7%) | 0 |
| Renal and urinary disorders | 1 (0.6%) | 2 (1.2%) |
| HLGT: Urolithiases | 1 (0.6%) | 2 (1.2%) |
| HLT: Renal lithiasis | 0 | 2 (1.2%) |
| Nephrolithiasis | 0 | 2 (1.2%) |
| General disorders and administration site conditions | 12 (7.5%) | 5 (3.1%) |
| HLGT: Administration site reactions | 5 (3.1%) | 1 (0.6%) |
| HLT: Injection site reactions | 5 (3.1%) | 1 (0.6%) |
| Injection site pruritus | 2 (1.2%) | 0 |
| HLGT: General system disorders NEC | 8 (5.0%) | 4 (2.5%) |
| HLT: Asthenic conditions | 7 (4.3%) | 0 |
| Asthenia | 2 (1.2%) | 0 |
| Fatigue | 5 (3.1%) | 0 |
| HLT: Oedema NBC | 1 (1.6%) | 3 (1.9%) |
| Oedema | 0 | 2 (1.2%) |
| Investigations | 3 (1.9%) | 5 (3.1%) |
| HLGT: Gastrointestinal investigations | 2 (1.2%) | 2 (1.2%) |
| HLT: Digestive enzymes | 2 (1.2%) | 2 (1.2%) |
| Lipase increased | 2 (1.2%) | 1 (0.6%) |
| Injury, poisoning and procedural complications | 7 (4.3%) | 11 (6.8%) |

TABLE 16-continued

Number (%) of patients with TEAE(s) that occurred with PT >=1% in any treatment group by primary SOC, HLGT, HLT and PT - Safety population

| PRIMARY SYSTEM ORGAN CLASS<br>HLGT: High Level Group Term<br>HLT: High Level Term<br>Preferred Term n (%) | Insulin<br>Glargine/Lixisenatide<br>Fixed Ratio<br>Combination<br>(N = 161) | Insulin<br>Glargine<br>(N = 162) |
|---|---|---|
| HLGT: Injuries NEC | 2 (1.2%) | 9 (5.6%) |
| HLT: Skin injuries NEC | 0 | 5 (3.1%) |
| Contusion | 0 | 2 (1.2%) |
| Laceration | 0 | 3 (1.9%) |

TEAE: Treatment emergent adverse event,
SOC: System organ class,
HLGT: High level group term,
HLT: High level term,
PT: Preferred term
MedDRA 15.1
n (%) = number and percentage of patients with at least one TEAE
Note:
Table sorted by SOC internationally agreed order and HLGT, HLT, PT by alphabetic order Only SOC with at least one PT 2:1% in at least one group are presented 3.3.2 Deaths, Serious Treatment-Emergent Adverse Events No deaths were reported in this study. The number of patients with treatment emergent SAE was 9 (5.6%) in the combination group and 6 (3.7%) in the insulin glargine group, which were distributed over a variety of SOCs without a notable increase in any specific SOC (table 17).

TABLE 17

Number (%) of patients with treatment emergent SAE presented by primary SOC, HLGT, HLT, and PT - Safety population

| PRIMARY SYSTEM ORGAN CLASS<br>HLGT: High Level Group Term<br>HLT: High Level Term<br>Preferred Term [n (%)] | Insulin<br>Glargine/Lixisenatide<br>Fixed Ratio<br>Combination<br>(N = 161) | Insulin<br>Glargine<br>(N = 162) |
|---|---|---|
| Any TEAE | 9 (5.6%) | 6 (3.7%) |
| Infections and infestations | 1 (0.6%) | 1 (0.6%) |
| HLGT: Bacterial infectious disorders | 1 (0.6%) | 0 |
| HLT: Bacterial infections NEC | 1 (0.6%) | 0 |
| Cellulitis | 1 (0.6%) | 0 |
| HLGT: Infections - pathogen unspecified | 0 | 1 (0.6%) |
| HLT: Urinary tract infections | 0 | 1 (0.6%) |
| Urinary tract infection | 0 | 1 (0.6%) |
| Neoplasms benign, malignant and unspecified (incl cysts and polyps) | 1 (0.6%) | 0 |
| HLGT: Reproductive neoplasms female malignant and unspecified | 1 (0.6%) | 0 |
| HLT: Ovarian neoplasms malignant (excl germ cell) | 1 (0.6%) | 0 |
| Ovarian cancer | 1 (0.6%) | 0 |
| Psychiatric disorders | 0 | 1 (0.6%) |
| HLGT: Depressed mood disorders and disturbances | 0 | 1 (0.6%) |
| HLT: Depressive disorders | 0 | 1 (0.6%) |
| Depression | 0 | 1 (0.6%) |
| Nervous system disorders | 2 (1.2%) | 1 (0.6%) |
| HLGT: Neurological disorders NEC | 0 | 1 (0.6%) |
| HLT: Neurological signs and symptoms NEC | 0 | 1 (0.6%) |
| Presyncope | 0 | 1 (0.6%) |
| HLGT: Peripheral neuropathies | 1 (0.6%) | 0 |
| HLT: Chronic polyneuropathies | 1 (0.6%) | 0 |
| Diabetic neuropathy | 1 (0.6%) | 0 |
| HLGT: Spinal cord and nerve root disorders | 1 (0.6%) | 0 |
| HLT: Lumbar spinal cord and nerve root disorders | 1 (0.6%) | 0 |
| Sciatica | 1 (0.6%) | 0 |
| Cardiac disorders | 3 (1.9%) | 1 (0.6%) |
| HLGT: Cardiac arrhythmias | 1 (0.6%) | 1 (0.6%) |
| HLT: Rate and rhythm disorders NEC | 1 (0.6%) | 0 |
| Bradycardia | 1 (0.6%) | 0 |
| HLT: Supraventricular arrhythmias | 0 | 1 (0.6%) |
| Atrial fibrillation | 0 | 1 (0.6%) |
| HLGT: Coronary artery disorders | 2 (1.2%) | 0 |
| HLT: Ischaemic coronary artery disorders | 2 (1.2%) | 0 |
| Angina pectoris | 1 (0.6%) | 0 |

TABLE 17-continued

Number (%) of patients with treatment emergent SAE presented by primary SOC, HLGT, HLT, and PT - Safety population

| PRIMARY SYSTEM ORGAN CLASS<br>HLGT: High Level Group Term<br>HLT: High Level Term<br>Preferred Term [n (%)] | Insulin Glargine/Lixisenatide Fixed Ratio Combination (N = 161) | Insulin Glargine (N = 162) |
|---|---|---|
| Angina unstable | 1 (0.6%) | 0 |
| Musculoskeletal and connective tissue disorders | 2 (1.2%) | 1 (0.6%) |
| HLGT: Joint disorders | 0 | 1 (0.6%) |
| HLT: Osteoarthropathies | 0 | 1 (0.6%) |
| Osteoarthritis | 0 | 1 (0.6%) |
| HLGT: Musculoskeletal and connective tissue deformities (incl intervertebral disc disorders) | 1 (0.6%) | 0 |
| HLT: Intervertebral disc disorders NEC | 1 (0.6%) | 0 |
| Intervertebral disc protrusion | 1 (0.6%) | 0 |
| HLGT: Musculoskeletal and connective tissue disorders NEC | 1 (0.6%) | 0 |
| HLT: Musculoskeletal and connective tissue pain and discomfort | 1 (0.6%) | 0 |
| Pain in extremity | 1 (0.6%) | 0 |
| Renal and urinary disorders | 1 (0.6%) | 0 |
| HLGT: Urolithiases | 1 (0.6%) | 0 |
| HLT: Urinary tract lithiasis (excl renal) | 1 (0.6%) | 0 |
| Calculus ureteric | 1 (0.6%) | 0 |
| Investigations | 0 | 1 (0.6%) |
| HLGT: Cardiac and vascular investigations (excl enzyme tests) | 0 | 1 (0.6%) |
| HLT: ECG investigations | 0 | 1 (0.6%) |
| ECG signs of myocardial ischaemia | 0 | 1 (0.6%) |
| Injury, poisoning and procedural complications | 1 (0.6%) | 0 |
| HLGT: Bone and joint injuries | 1 (0.6%) | 0 |
| HLT: Upper limb fractures and dislocations | 1 (0.6%) | 0 |
| Radius fracture | 1 (0.6%) | 0 |

SAE: Serious adverse event,
SOC: System organ class,
HLGT: High level group term,
HLT: High level term,
PT: Preferred term
MedDRA 15.1
n (%) = number and percentage of patients with at least one treatment emergent SAE
Note:
Table sorted by SOC internationally agreed order and HLGT, HLT, PT by alphabetic order

3.3.3 Adverse Events Leading to Withdrawal

Six patients (3.7%) in the combination group discontinued treatment due to TEAEs compared with none in the insulin glargine group (Table 18). For 2 of these patients, TEAEs leading to treatment discontinuation were those from the gastrointestinal disorders SOC (nausea and/or vomiting). One patient with nausea and vomiting and 1 patient with nausea and headache discontinued the IMP at days 66 and 53, and their last insulin daily dose was 52 U (lixisenatide 26 μg) and 18 U (lixisenatide 9 μg), respectively.

A patient with hypersensitivity discontinued the IMP on first dose day. This event was not positively adjudicated as an allergic reaction by ARAC. Confusional state and dizziness in each patient were confirmed as not related to symptomatic hypoglycemia.

TABLE 18

Number (%) of patients experiencing TEAE(s) leading to permanent treatment discontinuation by primary SOC, HLGT, HLT, and PT during on-treatment period - Safety population

| PRIMARY SYSTEM ORGAN CLASS<br>HLGT: High Level Group Term<br>HLT: High Level Term<br>Preferred Term [n (%)] | Insulin Glargine/Lixisenatide Fixed Ratio Combination (N = 161) | Insulin Glargine (N = 162) |
|---|---|---|
| Any TEAE | 6 (3.7%) | 0 |
| Neoplasms benign, malignant and unspecified (incl cysts and polyps) | 1 (0.6%) | 0 |
| HLGT: Reproductive neoplasms female malignant and unspecified | 1 (0.6%) | 0 |
| HLT: Ovarian neoplasms malignant (excl germ cell) | 1 (0.6%) | 0 |
| Ovarian cancer | 1 (0.6%) | 0 |
| Immune system disorders | 1 (0.6%) | 0 |
| HLGT: Allergic conditions | 1 (0.6%) | 0 |

TABLE 18-continued

Number (%) of patients experiencing TEAE(s) leading to permanent treatment discontinuation by primary SOC, HLGT, HLT, and PT during on-treatment period - Safety population

| PRIMARY SYSTEM ORGAN CLASS<br>HLGT: High Level Group Term<br>HLT: High Level Term<br>Preferred Term [n (%)] | Insulin Glargine/Lixisenatide Fixed Ratio Combination (N = 161) | Insulin Glargine (N = 162) |
|---|---|---|
| HLT: Allergic conditions NEC | 1 (0.6%) | 0 |
| Hypersensitivity | 1 (0.6%) | 0 |
| Psychiatric disorders | 1 (0.6%) | 0 |
| HLGT: Deliria (incl confusion) | 1 (0.6%) | 0 |
| HLT: Confusion and disorientation | 1 (0.6%) | 0 |
| Confusional state | 1 (0.6%) | 0 |
| Nervous system disorders | 2 (1.2%) | 0 |
| HLGT: Headaches | 1 (0.6%) | 0 |
| HLT: Headaches NEC | 1 (0.6%) | 0 |
| Headache | 1 (0.6%) | 0 |
| HLGT: Neurological disorders NEC | 1 (0.6%) | 0 |
| HLT: Neurological signs and symptoms NEC | 1 (0.6%) | 0 |
| Dizziness | 1 (0.6%) | 0 |
| Gastrointestinal disorders | 2 (1.2%) | 0 |
| HLGT: Gastrointestinal signs and symptoms | 2 (1.2%) | 0 |
| HLT: Nausea and vomiting symptoms | 2 (1.2%) | 0 |
| Nausea | 2 (1.2%) | 0 |
| Vomiting | 1 (0.6%) | 0 |

TEAE: Treatment emergent adverse event,
SOC: System organ class,
HLGT: High level group term,
HLT: High level term,
PT: Preferred term
MedDRA 15.1
n (%) = number and percentage of patients with at least one TEAE leading to permanent treatment discontinuation
Note:
Table sorted by SOC internationally agreed order and HLGT, HLT, PT by alphabetic order Hypersensitivity: it was adjudicated as not allergic event by ARAC.

3.3.4 Other Significant Adverse Events

A total of 6 patients (5 patients in the combination group and 1 patient in the insulin glargine group) experienced injection site reactions (Table 19). None of these reactions were considered serious or severe or led to treatment discontinuation.

TABLE 19

Number (%) of patients experiencing injection site reactions during the TEAE period - Safety population

| Event source<br>Preferred Term | Insulin Glargine/ Lixisenatide Fixed Ratio Combination (N = 161) | Insulin Glargine (N = 162) |
|---|---|---|
| Any injection site reactions | 5 (3.1%) | 1 (0.6%) |
| PTs coded from the investigator reported terms | 5 (3.1%) | 1 (0.6%) |
| Injection site pruritus | 2 (1.2%) | 0 |
| Injection site pain | 1 (0.6%) | 1 (0.6%) |
| Injection site rash | 1 (0.6%) | 0 |
| Injection site urticaria | 1 (0.6%) | 0 |
| PTs coded from the ARAC diagnosis terms | 1 (0.6%) | 0 |
| Injection site reaction | 1 (0.6%) | 0 |

ARAC = Allergic Reaction Assessment Committee.
PT = Preferred Term.

A total of 2 patients (1 [0.6%] in each group) reported 6 events positively adjudicated as allergic reactions by the ARAC with the same diagnosis of allergic rhinitis. None was adjudicated as possibly related to the IMP (table 20).

TABLE 20

Number (%) of patients with events adjudicated as allergic reaction by ARAC during the TEAE period - Safety population

| Relationship to study treatment (by ARAC) | MedDRA coded term (PT) for ARAC diagnosis | ARAC diagnosis | Insulin Glargine/ Lixisenatide Fixed Ratio Combination (N = 161) | Insulin Glargine (N = 162) |
|---|---|---|---|---|
| All | Events adjudicated as an allergic reaction by ARAC | | | |
| | Rhinitis allergic | ALLERGIC RHINITIS | 1 (0.6%)<br>1 (0.6%) | 1 (0.6%)<br>1 (0.6%) |
| Not related to IMP | Events adjudicated as an allergic reaction by ARAC | | | |
| | Rhinitis allergic | ALLERGIC RHINITIS | 1 (0.6%)<br>1 (0.6%) | 1 (0.6%)<br>1 (0.6%) |

ARAC = Allergic Reaction Assessment Committee.
IMP = Investigational medicinal product.

Per protocol, any increase in amylase and/or lipase above twice the upper limit of normal range (ULN) or in Calcitonin ≥20 pg/mL that had been confirmed by a repeat measurement was to be monitored and documented on a specific AE form. During treatment period, 3 patients (2 [1.2%] in the combination group and 1 [0.6%] in the insulin glargine group) had a TEAE of lipase increased (>2 ULN) and 1 patient (in the insulin glargine group) had a TEAE of amylase increased (>2 ULN) that were reported on the specific AE form. No patients reported a TEAE of increased calcitonin (≥20 pg/mL).

The number of patients who had at least 1 value of lipase or amylase ULN, or at least 1 value of calcitonin ≥20 pg/ml during the on-treatment period was also summarized. One patient in the insulin glargine group had at least 1 value of amylase ≥3 ULN, and 5 patients (4 in the combination group and 1 in the insulin glargine group) had at least 1 value of lipase ≥3 ULN. One patient in the insulin glargine group had 1 value of calcitonin ≥20 pg/ml (but <50 pg/ml) with retested values within the normal range.

One patient in the combination group and one patient in the insulin had respectively two events (hospitalization for unstable angina and percutaneous coronary intervention (PCI]) and one event (PCI) adjudicated as major cardiovascular events by cardiovascular events adjudication committee (CAC).

3.3.5 Other Safety Observation-Symptomatic Hypoglycemia

Symptomatic hypoglycemia events (including documented, probable, and severe symptomatic hypoglycemia) were reported in 40 (24.8%) patients treated with the combination compared to 40 (24.7%) insulin glargine treated patients. The number of symptomatic hypoglycemia events per patient-year was 1.11 in both treatment groups. No severe symptomatic hypoglycemia was reported in any group (Table 21).

The rate of documented symptomatic hypoglycemia with plasma glucose ≤70 mg/dL (3.9 mmol/L) was similar in both treatment groups (35 [21.7%] versus 37 [22.8%] in the combination and insulin glargine groups, respectively). For documented symptomatic hypoglycemia with plasma glucose <60 mg/dL (3.3 mmol/L) the rate was higher in the combination group versus the insulin glargine group [20 (12.4%) versus 9 (5.6%)].

TABLE 21

Summary of symptomatic hypoglycemia recorded on the dedicated eCRF and meeting protocol definition during the TEAE period - Safety population

| Type | Insulin Glargine/ Lixisenatide Fixed Ratio Combination (N = 161) | Insulin Glargine (N = 162) |
| --- | --- | --- |
| Total patient years | 73.1 | 75.6 |
| Symptomatic hypoglycemia | | |
| Number of patients with events, n (%) | 40 (24.8%) | 40 (24.7%) |
| Number of events | 81 | 84 |
| Number of events per 100 patient years[a] | 110.8 | 111.1 |
| Documented symptomatic hypoglycemia (plasma glucose <=70 mg/dL [3.9 mmol/L]) | | |
| Number of patients with events, n (%) | 35 (21.7%) | 37 (22.8%) |
| Number of events | 71 | 79 |
| Number of events per 100 patient years[a] | 97.1 | 104.5 |
| Documented symptomatic hypoglycemia (plasma glucose <60 mg/dL [3.3 mmol/L]) | | |
| Number of patients with events, n (%) | 20 (12.4%) | 9 (5.6%) |
| Number of events | 30 | 18 |
| Number of events per 100 patient years[a] | 41.0 | 23.8 |
| Documented symptomatic hypoglycemia (plasma glucose <54 mg/dL [3.0 mmol/L]) | | |
| Number of patients with events, n (%) | 13 (8.1%) | 4 (2.5%) |
| Number of events | 16 | 10 |
| Number of events per 100 patient years[a] | 21.9 | 13.2 |

TABLE 21-continued

Summary of symptomatic hypoglycemia recorded on the dedicated eCRF and meeting protocol definition during the TEAE period - Safety population

| Type | Insulin Glargine/ Lixisenatide Fixed Ratio Combination (N = 161) | Insulin Glargine (N = 162) |
| --- | --- | --- |
| Probable symptomatic hypoglycemia | | |
| Number of patients with events, n (%) | 9 (5.6%) | 5 (3.1%) |
| Number of events | 10 | 5 |
| Number of events per 100 patient years[a] | 13.7 | 6.6 |
| Severe symptomatic hypoglycemia | | |
| Number of patients with events, n (%) | 0 | 0 |
| Number of events | 0 | 0 |
| Number of events per 100 patient years[a] | 0.0 | 0.0 |

[a]Calculated as (number of events * 100 divided by total exposure + 3 days in patient years). Symptomatic hypoglycemia = symptomatic hypoglycemia recorded on the dedicated eCRF and meeting protocol definition for severe, or documented, or probable symptomatic hypoglycemia.

EXAMPLE 2

A randomized, 30 week, active-controlled, open-label, 3-treatment arm, parallel-group multicenter study comparing the efficacy and safety of insulin glargine/lixisenatide fixed ratio combination to insulin glargine alone and to lixisenatide alone on top of metformin in patients with T2DM.

Compound code: HOE901/AVE0010

Study Title & Name

Title: A randomized, 30 week, active-controlled, open-label, 3-treatment arm, parallel group multicenter study comparing the efficacy and safety of insulin glargine/lixisenatide fixed ratio combination to insulin glargine alone and to lixisenatide alone on top of metformin in patients with T2DM.

Short Title: Efficacy and safety of insulin glargine/lixisenatide fixed ratio combination versus insulin glargine alone and versus lixisenatide alone on top of metformin in patients with T2DM.

Medical Condition

| Therapeutic area | MedDRA Preferred Term | MedDRA classification code |
| --- | --- | --- |
| Nutritional and metabolic diseases | Type 2 diabetes | 10067585 |

Study Objectives

Primary: To compare the insulin glargine/lixisenatide fixed ratio combination versus lixisenatide and versus insulin glargine (on top of metformin treatment) in HbA1c change from baseline to week 30.

Secondary: To compare the overall efficacy and safety of insulin glargine/lixisenatide fixed ratio combination versus insulin glargine and lixisenatide alone (on top of metformin treatment) over a 30 week treatment period in patients with type 2 diabetes

| Primary purpose: | Treatment | Primary focus: | Safety/Efficacy |
|---|---|---|---|

Scope of the Trial:

| [ ] Diagnosis | [ ] Prophylaxis | [X] Therapy | [X] Efficacy |
|---|---|---|---|
| [X] Safety | [ ] Pharmacodynamic | [X] Pharmacokinetic | [ ] Bioequivalence |
| [ ] Dose response | [ ] Pharmacogenetic | [ ] Pharmacogenomic | [ ] Pharmacoeconomic |

Study Design

| Phase: | Phase 3 | Allocation: | Randomized |
|---|---|---|---|
| Masking: | Open Label | Design: | Parallel |

Number of arms: 3

| Arm Label Label in study schema | Arm description Provide information specific to the arm -in particular details on the IMP and non-IMP administration (e.g. product, dosage, frequency, duration, condition of the intake(s)) | Arm type Select "experimental" when the study compound is administered |
|---|---|---|
| Insulin glargine/lixisenatide fixed ratio combination | Insulin glargine/lixisenatide fixed ratio combination is injected subcutaneously s.c. (under the skin) once daily (OD). Dose individually adjusted. Metformin treatment should be continued. | Experimental |
| Insulin glargine | Insulin glargine is injected subcutaneously s.c. (under the skin) once daily (OD). Dose individually adjusted. Metformin treatment should be continued. | Active Comparator |
| Lixisenatide | Lixisenatide is injected subcutaneously s.c. (under the skin) once daily (OD). Starting dose will be 10 µg, the increased to the 20 µg maintenance dose after 2 weeks. Metformin treatment should be continued. | Active Comparator |

The insulin glargine/lixisenatide fixed ratio combination comprises 100 U/mL insulin glargine and 50 µg/mL lixisenatide. The insulin glargine formulation (Lantus®) comprises 100 U/ml insulin glargine. The lixisenatide formulation (Lyxumia®) comprises 50 µg/ml lixisenatide (for administration of a dose of 10 µg lixisenatide) or 100 µg/ml lixisenatide (for administration of a dose of 20 µg lixisenatide). Metformin is administered in a dose of at least 1.0 g/day or at least 1.5 g/day.

Study Population

| | | Age Range | |
|---|---|---|---|
| Population | Gender | Minimum | Maximum |
| [ ] Healthy volunteers | Both | 18 Unit: Years | Unit: Select Unit |
| [X] Patients | | or [ ] NA (no limit) | or [X] NA (no limit) |

Inclusion Criteria:

Patients with type 2 diabetes mellitus diagnosed for at least 1 year before the screening visit, treated for at least 3 months prior to visit 1 with metformin alone or metformin and a second oral anti-diabetic treatment that can be a sulfonylurea (SU) or a glinide, or a SGLT-2 inhibitor who are not adequately controlled with this treatment;

Signed written informed consent

Exclusion Criteria:

Age under legal age of adulthood at screening visit;

HbA1c at screening visit:

<7.5% and >10% for patients previously treated with metformin alone,

<7.0% and >9% for patients previously treated with metformin and a second oral anti-diabetic treatment;

Pregnancy or lactation, women of childbearing potential with no effective contraceptive method;

Use of other oral or injectable glucose-lowering agents than stated in the inclusion criteria in a period of 3 months prior to screening.

Treatment with insulin more than 3 months ago (except for short-term treatment due to intercurrent illness including gestational diabetes at the discretion of the trial physician)

History of discontinuation of a previous treatment with a GLP-1 receptor agonist (GLP-1 RA) due to safety/tolerability issue or lack of efficacy;

Patient who has previously participated in any clinical trial with lixisenatide or the insulin glargine/lixisenatide fixed ratio combination or has previously received lixisenatide.

Any contraindication to metformin use, according to local labeling

Use of weight loss drugs within 3 months prior to screening visit.

Within the last 6 months prior to screening visit: history of stroke, myocardial infarction, unstable angina, or heart failure requiring hospitalization. Planned coronary, carotid or peripheral artery revascularisation procedures to be performed during the study period.

History of pancreatitis (unless pancreatitis was related to gallstones and cholecystectomy was already performed), chronic pancreatitis, pancreatitis during a previous treatment with incretin therapies, pancreatectomy, stomach/gastric surgery.

Personal or immediate family history of medullary thyroid cancer (MTC) or genetic conditions that predispose to MTC (eg, multiple endocrine neoplasia syndromes).

Uncontrolled or inadequately controlled hypertension (systolic blood pressure above 180 mmHg or diastolic blood pressure above 95 mmHg) at screening visit At screening visit, Body Mass Index (BMI) less than or equal to 20 or above 35 kg/m$^2$ At screening visit amylase and/or lipase more than 3 times the upper limit of the normal (ULN) laboratory range, At screening visit ALT or AST more than 3 ULN At screening visit calcitonin above or equal to 20 μg/mL (5.9 pmol/L)

Exclusion Criteria for Randomization at the End of the Screening Period:

HbA1c <7% or >10% at visit 4 (week 1);

Fasting Plasma glucose at visit 4 (week −1) >250 mg/dL (13.9 mmol/L);

Metformin maximal tolerated dose <1500 mg/day;

Amylase and/or lipase measured one week prior to randomization is >3 times ULN;

Specific Vulnerable Populations:

[X] Women of child-bearing potential not using contraception

[X] Women of child-bearing potential using contraception

[ ] Pregnant women     [ ] Nursing women     [ ] Emergency situation

Total Expected Number of Subjects/Patients

|  | Included/Enrolled (Inform Consent Form signed) | Randomized* |
|---|---|---|
| Planned number of subjects/patients | 2200 | 1125 |

*treated for non randomized studies

Approximate number of subjects/patients per age range:

| Adults: 920 (18-64 years) | Elderly: 205 (≥65 years) |
|---|---|

Medicinal Products (Investigational & Non-Investigational)

| INN if available or placebo | Compound code Sanofi compound only | Trade name If available | Pharmaceutical form e.g. tablet, capsule, solution . . . | Route of administration e.g. oral, intravenous, intramuscular, subcutaneous . . . |
|---|---|---|---|---|
| Insulin glargine/lixisenatide | HOE901/AVE0010 | | solution for injection (disposable self injector) | subcutaneous injection |
| Insulin glargine | HOE901 | Lantus ® | solution for injection (disposable self injector) | subcutaneous injection |
| Lixisenatide | AVE0010 | Lyxumia ® | solution for injection (disposable self injector) | subcutaneous injection |

Endpoints

| Endpoint title e.g. change from baseline in a parameter, time to a specific event, number of patients with prespecified event, specific measurement | Time frame for evaluation Enter the timepoints at which the measure is assessed or the assessment duration | Assess a safety issue? |
|---|---|---|
| Primary Endpoint | | |
| Change in HbA1c from baseline | week 30 | [ ] Yes [ ] Yes [ ] Yes |

| Secondary Endpoints | | |
|---|---|---|
| Percentage of patients reaching HbA1c targets | week 30 | [ ] Yes |
| | | [ ] Yes |
| Change in 2-hour Post Prandial Glucose and in blood glucose excursion during standardized meal test from baseline | week 30 | [ ] Yes |
| Change in body weight from baseline | week 30 | [ ] Yes |
| Change in 7-point Self Measured Plasma Glucose profiles from baseline | week 30 | [ ] Yes |

| | | |
|---|---|---|
| Change in daily dose of insulin glargine from baseline | week 30 | [ ] Yes |
| Change in FPG from baseline | week 30 | [ ] Yes |

| | | |
|---|---|---|
| Documented (plasma glucose less than or equal to 70 mg/dl) symptomatic hypoglycemia | week 30 | [X] Yes |
| Severe symptomatic hypoglycemia | week 30 | [X] Yes |
| | | [ ] Yes |

Duration of Study Period

| | |
|---|---|
| Duration per subject/patient: | approximately 37 weeks including 30 week treatment period |

The invention claimed is:

1. A method for improving glycemic control in a patient with type 2 diabetes mellitus inadequately controlled by treatment with insulin glargine and metformin, the method comprising administering to the patient in need thereof a therapeutically effective amount of a fixed ratio combination of:
   (a) lixisenatide or a pharmaceutically acceptable salt thereof, and
   (b) insulin glargine or a pharmaceutically acceptable salt thereof,
   wherein the fixed ratio combination is administered as a single daily injection;
   wherein the patient has been treated with metformin at a stable dose of at least 1.5 g per day for at least 3 months and has a HbA1c level between 7% and 10%;
   such that the administration of the fixed ratio combination improves glycemic control in the patient over treatment with insulin glargine and metformin.

2. The method of claim 1, wherein the improvement in glycemic control is a reduction of HbA1c levels in the patient.

3. The method of claim 1, wherein the improvement in glycemic control is a reduction of post-prandial glucose (PPG) levels in the patient.

* * * * *

SEQUENCE LISTING

```
<160> NUMBER OF SEQ ID NOS: 2

<210> SEQ ID NO 1
<211> LENGTH: 44
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (44)..(44)
<223> OTHER INFORMATION: C-terminal amide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (39)..(39)
<223> OTHER INFORMATION: C-terminal amide

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35
```